US010251971B2

(12) United States Patent
Roy et al.

(10) Patent No.: US 10,251,971 B2
(45) Date of Patent: Apr. 9, 2019

(54) COMPOSITIONS AND METHODS FOR MULTIPURPOSE DISINFECTION AND STERILIZATION SOLUTIONS

(71) Applicant: The Administrators of the Tulane Educational Fund, New Orleans, LA (US)

(72) Inventors: Chad Roy, Madisonville, LA (US); Rebecca Metzinger, New Orleans, LA (US); Robert Reimers, Houston, TX (US)

(73) Assignee: THE ADMINISTRATORS OF THE TULANE EDUCATIONAL FUND, New Orleans, LA (US)

( * ) Notice: Subject to any disclaimer, the term of this patent is extended or adjusted under 35 U.S.C. 154(b) by 0 days.

(21) Appl. No.: 15/256,299

(22) Filed: Sep. 2, 2016

(65) Prior Publication Data
US 2017/0065738 A1    Mar. 9, 2017

Related U.S. Application Data

(60) Provisional application No. 62/213,964, filed on Sep. 3, 2015.

(51) Int. Cl.
A61L 12/10    (2006.01)
A61L 12/14    (2006.01)
A61L 2/18     (2006.01)
A61L 2/00     (2006.01)

(52) U.S. Cl.
CPC .............. *A61L 12/10* (2013.01); *A61L 2/0088* (2013.01); *A61L 2/18* (2013.01); *A61L 12/102* (2013.01); *A61L 12/142* (2013.01); *A61L 12/143* (2013.01); *A61L 12/145* (2013.01); A61L 2202/24 (2013.01)

(58) Field of Classification Search
CPC ....................................................... A61L 12/10
See application file for complete search history.

(56) References Cited

U.S. PATENT DOCUMENTS

| 3,873,696 | A | * | 3/1975 | Randeri ................. A61L 12/08 252/188.1 |
| 4,499,077 | A |   | 2/1985 | Stockel et al. |
| 4,654,208 | A | * | 3/1987 | Stockel ................. A01N 59/00 424/429 |
| 5,320,806 | A | * | 6/1994 | Dziabo ................. A61L 12/102 134/901 |
| 5,611,938 | A |   | 3/1997 | Smolik et al. |
| 5,622,725 | A |   | 4/1997 | Kross |
| 5,782,992 | A |   | 7/1998 | Frangione |
| 6,083,457 | A |   | 7/2000 | Parkinson et al. |
| 7,618,655 | B2 |  | 11/2009 | Wannowius et al. |
| 2002/0053657 | A1 |  | 5/2002 | Parkinson et al. |
| 2003/0129083 | A1 | * | 7/2003 | Graham ................ A01N 47/44 422/42 |
| 2003/0228996 | A1 |  | 12/2003 | Hei et al. |
| 2004/0120916 | A1 |  | 6/2004 | Huth |
| 2005/0013763 | A1 |  | 1/2005 | Bober et al. |
| 2005/0155937 | A1 | * | 7/2005 | Zawada ................ A01N 33/12 210/758 |
| 2005/0227902 | A1 |  | 10/2005 | Erazo-Majewicz et al. |
| 2008/0213391 | A1 |  | 9/2008 | Kaiser et al. |
| 2008/0226748 | A1 |  | 9/2008 | Stevenson |
| 2009/0155188 | A1 |  | 6/2009 | Austin et al. |
| 2010/0040565 | A1 |  | 2/2010 | Homola et al. |
| 2010/0055196 | A1 |  | 3/2010 | MacGregor |
| 2010/0258033 | A1 |  | 10/2010 | Yang et al. |
| 2010/0322890 | A1 | * | 12/2010 | Edwards ................ A01N 33/12 424/78.08 |
| 2011/0052655 | A1 |  | 3/2011 | Whitekettle et al. |
| 2011/0189112 | A1 |  | 8/2011 | Full |
| 2012/0046556 | A1 |  | 2/2012 | Block |
| 2012/0263657 | A1 |  | 10/2012 | Doyle et al. |
| 2012/0322124 | A1 |  | 12/2012 | Okull et al. |
| 2013/0165572 | A1 |  | 6/2013 | Scheuing et al. |
| 2014/0116917 | A1 |  | 5/2014 | Scheuing et al. |
| 2015/0250820 | A1 |  | 9/2015 | Kaiser et al. |
| 2015/0305343 | A1 |  | 10/2015 | Burke et al. |
| 2015/0306266 | A1 |  | 10/2015 | Burke et al. |
| 2015/0373986 | A1 |  | 12/2015 | Burke et al. |
| 2016/0030618 | A1 |  | 2/2016 | Samani et al. |

FOREIGN PATENT DOCUMENTS

| EP | 1408005 A2 | 4/2004 |
| EP | 1557088 A1 | 7/2005 |
| EP | 1969938 A2 | 9/2008 |
| EP | 1850913 B1 | 9/2009 |
| EP | 2283728 A2 | 2/2011 |
| WO | WO-9109632 A1 | 7/1991 |
| WO | WO-9304706 A1 | 3/1993 |

(Continued)

OTHER PUBLICATIONS

PCT/US2016/50266 International Search Report and Written Opinion dated Nov. 28, 2016.

*Primary Examiner* — Adam C Milligan
*Assistant Examiner* — Sarah Alawadi
(74) *Attorney, Agent, or Firm* — Wilson Sonsini Goodrich & Rosati

(57) ABSTRACT

The present disclosure discloses compositions and methods for multipurpose disinfection and sterilization solutions broadly effective against multiple microbial pathogens. The present disclosure demonstrates broad spectrum antimicrobial activity against environmental and pathogenic amoeba, bacterial spores, vegetative bacteria, fungi, rickettsia, viruses, parasites and toxic microbial products. The multipurpose disinfection solutions of the present disclosure may be used alone or in combination for a variety of purposes, including disinfection of medical devices such as contact lenses, contact lens cases, surgical instruments, and dental instruments.

9 Claims, 15 Drawing Sheets

(56) References Cited

FOREIGN PATENT DOCUMENTS

| | | |
|---|---|---|
| WO | WO-9614092 A1 | 5/1996 |
| WO | WO-9639030 A1 | 12/1996 |
| WO | WO-9709267 A1 | 3/1997 |
| WO | WO-0057703 A1 | 10/2000 |
| WO | WO-02062142 A1 | 8/2002 |
| WO | WO-2004094305 A2 | 11/2004 |
| WO | WO-2004101432 A2 | 11/2004 |
| WO | WO-2005063308 A1 | 7/2005 |
| WO | WO-2006000756 A1 | 1/2006 |
| WO | WO-2006085975 A2 | 8/2006 |
| WO | WO-2006113166 A1 | 10/2006 |
| WO | WO-2007027859 A1 | 3/2007 |
| WO | WO-2008011836 A2 | 1/2008 |
| WO | WO-2008083256 A2 | 7/2008 |
| WO | WO-2008092006 A2 | 7/2008 |
| WO | WO-2010019491 A1 | 2/2010 |
| WO | WO-2010091066 A2 | 8/2010 |
| WO | WO-2011094657 A2 | 8/2011 |
| WO | WO-2011123297 A1 | 10/2011 |
| WO | WO-2012042243 A1 | 4/2012 |
| WO | WO-2012122395 A2 | 9/2012 |
| WO | WO-2012136968 A1 | 10/2012 |
| WO | WO-2013032961 A1 | 3/2013 |
| WO | WO-2013106455 A1 | 7/2013 |
| WO | WO-2014070202 A1 | 5/2014 |
| WO | WO-2015073170 A1 | 5/2015 |
| WO | WO-2015105852 A1 | 7/2015 |
| WO | WO-2015112667 A1 | 7/2015 |
| WO | WO-2015112671 A1 | 7/2015 |
| WO | WO-2015120216 A1 | 8/2015 |
| WO | WO-2015157610 A1 | 10/2015 |
| WO | WO-2015167642 A1 | 11/2015 |
| WO | WO-2015167643 A1 | 11/2015 |
| WO | WO-2015167644 A1 | 11/2015 |
| WO | WO-2017041038 A1 | 3/2017 |

\* cited by examiner

FIG. 1

| MPDS | Antimicrobial agents | Surfactant, isotonic and buffering agents |
|---|---|---|
| SOL01 (SL1) | 0.01% Stabilized chlorine dioxide<br>0.002% C12-C14 alkyl(ethylbenzyl)dimethylammonium chloride<br>0.005% ammonium chloride | Deionized water |
| SOL02 (SL2) | 0.01% Stabilized chlorine dioxide<br>0.002% C12-C14 alkyl(ethylbenzyl)dimethylammonium chloride<br>0.005% ammonium chloride<br>0.0005% peracetic acid | Deionized water |

FIG. 3

| MPDS | Contact Time | Pa | Sa | Sm | Ca | Fs |
|---|---|---|---|---|---|---|
| | inoculating conc (CFU/ml) | 4.5E+05 | 1.03E+06 | 1.0E+08 | 7.9E+06 | 3.9E+05 |
| | 1 hr | CFU (log reduction) | | | | |
| SL1 | | 0 (>5) | 0 (>6) | 0 (>8) | 0 (>6) | 0 (>5) |
| SL2 | | 0 (>5) | 0 (>6) | 0 (>8) | 0 (>6) | 0 (>5) |
| ReNu | | TNTC (0) | TNTC (0) | 19 (7) | TNTC (0) | 134 (4) |
| Opti-Free | | TNTC (0) | TNTC (0) | TNTC (0) | TNTC (0) | 2 (5) |
| BioTrue | | TNTC (0) | TNTC (0) | 55 (7) | 26 (6) | 1 (5) |
| | 4 hr | CFU (log reduction) | | | | |
| SL1 | | 0 (>5) | 0 (>6) | 0 (>8) | 0 (>6) | 0 (>5) |
| SL2 | | 0 (>5) | 0 (>6) | 0 (>8) | 0 (>6) | 0 (>5) |
| ReNu | | TNTC (0) | TNTC (0) | 34 (7) | 52 (6) | 4 (5) |
| Opti-Free | | TNTC (0) | TNTC (0) | 79 (7) | 164 (5) | 0 (>5) |
| BioTrue | | TNTC (0) | TNTC (0) | 3 (8) | 13 (6) | 0 (>5) |

COMPOSITIONS AND METHODS FOR MULTIPURPOSE DISINFECTION AND STERILIZATION SOLUTIONS

CROSS REFERENCE

This application claims the benefit of U.S. Provisional Application No. 62/213,964 filed Sep. 3, 2015, the content of which is hereby incorporated by reference in its entirety.

BACKGROUND

The United States Centers for Disease Control and Prevention have reported that the annual direct hospital costs of treating healthcare-associated infections in the United States range from $35.7B to $45B. The most frequent nosocomial infections are surgical site infections, hepatitis B virus infections, septicemia, gastroenteritis, hepatitis C virus infections, urinary tract infections, and meningitis. Microbial agents responsible for these infections include *Acinetobacter, Burkholderia cepacia, Clostridium difficile, Clostridium sordellii*, Enterobacteriaceae, hepatitis B virus, hepatitis C virus, human immunodeficiency virus, influenza viruses, *Klebsiella, Staphylococcus aureus Mycobacterium abscessus*, norovirus, *Pseudomonas aeruginosa, Staphylococcus aureus, Mycobacterium tuberculosis*, vancomycin-intermediate *Staphylococcus aureus*, vancomycin-resistant *Staphylococcus aureus*, and vancomycin-resistant Enterococci.

While certain novel features of this disclosure shown and described below are pointed out in the claims, the disclosure is not intended to be limited to the details specified, since a person of ordinary skill in the relevant art will understand that various omissions, modifications, substitutions and changes in the forms and details of the disclosure illustrated and in its operation may be made without departing in any way from the spirit of the present disclosure. No feature of the disclosure is critical or essential unless it is expressly stated as being "critical" or "essential."

BRIEF SUMMARY OF THE INVENTION

The present disclosure provides novel chemical formulations and compositions for multiple uses including but not limited to disinfection of contact lenses, contact cases, medical devices, other medical/paramedical devices, and dental instruments.

Disclosed herein are methods of disinfection and sterilization utilizing the presently-disclosed compositions broadly effective against multiple microbial pathogens.

Disclosed herein is a medical disinfecting composition comprising (a) a chlorite salt; (b) a quaternary ammonium salt; (c) ammonium chloride; and (d) water. In some embodiments of a medical disinfecting composition, the chlorite salt is an alkali metal chlorite salt. In some embodiments, the alkali metal chlorite salt is sodium chlorite. In some embodiments of a medical disinfecting composition, the sodium chlorite is present in an amount ranging from about 0.0001% to about 0.1% (w/w). In some embodiments of a medical disinfecting composition, the sodium chlorite is provided as a stabilized chlorine dioxide solution. In some embodiments of a medical disinfecting composition, the stabilized chlorine dioxide is present in an amount ranging from about 0.005% to about 1.0% (w/w). In some embodiments of a medical disinfecting composition, the stabilized chlorine dioxide solution comprises chlorine dioxide. In some embodiments of a medical disinfecting composition, the quaternary ammonium salt comprises C12 or C14 alkyl chain. In some embodiments, the quaternary ammonium salt is not benzalkonium chloride. In some embodiments of a medical disinfecting composition, the quaternary ammonium salt is C12-C14-alkyl(ethylbenzyl)dimethylammonium chloride. In some embodiments of a medical disinfecting composition, the C12-C14-alkyl(ethylbenzyl)dimethylammonium chloride is present in an amount ranging from about 0.00005% to about 0.1% (w/w). In some embodiments of a medical disinfecting composition, the C12-C14-alkyl(ethylbenzyl)dimethylammonium chloride is present in an amount ranging from about 0.001% to about 0.1% (w/w). In some embodiments of a medical disinfecting composition, the ammonium chloride is present in an amount ranging from about 0.001% to about 2.0% (w/w). In some embodiments of a medical disinfecting composition, the composition further comprises a buffer to maintain the pH between about 7 and about 8. In some embodiments of a medical disinfecting composition, the pH is about 7.

Also disclosed herein is a method of disinfecting a medical device comprising contacting the medical device with a medical disinfecting composition comprising: (a) a chlorite salt; (b) a quaternary ammonium salt; (c) ammonium chloride; and (d) water. In some embodiments of a method of disinfecting a medical device, the chlorite salt is an alkali metal chlorite salt.

In some embodiments of a method of disinfecting a medical device, the alkali metal chlorite salt is sodium chlorite. In some embodiments of a method of disinfecting a medical device, the sodium chlorite is present in an amount ranging from about 0.0001% to about 0.1% (w/w). In some embodiments of a method of disinfecting a medical device, the sodium chlorite is provided as a stabilized chlorine dioxide solution. In some embodiments of a method of disinfecting a medical device, the stabilized chlorine dioxide is present in an amount ranging from about 0.005% to about 1.0% (w/w). In some embodiments of a method of disinfecting a medical device, the stabilized chlorine dioxide solution comprises chlorine dioxide.

In some embodiments of a method of disinfecting a medical device, the quaternary ammonium salt is not benzalkonium chloride. In some embodiments of a method of disinfecting a medical device, the quaternary ammonium salt is C12-C14-alkyl(ethylbenzyl)dimethylammonium chloride. In some embodiments of a method of disinfecting a medical device, the C12-C14-alkyl(ethylbenzyl)dimethylammonium chloride is present in an amount ranging from about 0.00005% to about 0.1% (w/w). In some embodiments of a method of disinfecting a medical device, the C12-C14-alkyl(ethylbenzyl)dimethylammonium chloride is present in an amount ranging from about 0.001% to about 0.1% (w/w). In some embodiments of a method of disinfecting a medical device, the ammonium chloride is present in an amount ranging from about 0.001% to about 2.0% (w/w). In some embodiments of a method of disinfecting a medical device, the method further comprises a buffer to maintain the pH between about 7 and about 8.

In some embodiments of a method of disinfecting a medical device, the medical device is in contact with a mammal tissue after contacting the medical device with a medical disinfecting composition. In some embodiments of a method of disinfecting a medical device, the medical device is selected from the group consisting of contact lenses, contact lens cases, surgical instruments, and dental instruments.

Other objects and advantages of this disclosure will become readily apparent from the ensuing description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the description of specific embodiments presented herein.

FIG. 1 shows formulations of two multipurpose disinfection solutions (SOL01 and SOL02).

FIG. 3 shows the antimicrobial activity of the two presently-disclosed multipurpose disinfection solutions (SOL01 and SOL02) and three commercially available multipurpose disinfection solutions.

DETAILED DESCRIPTION

Figure 2:
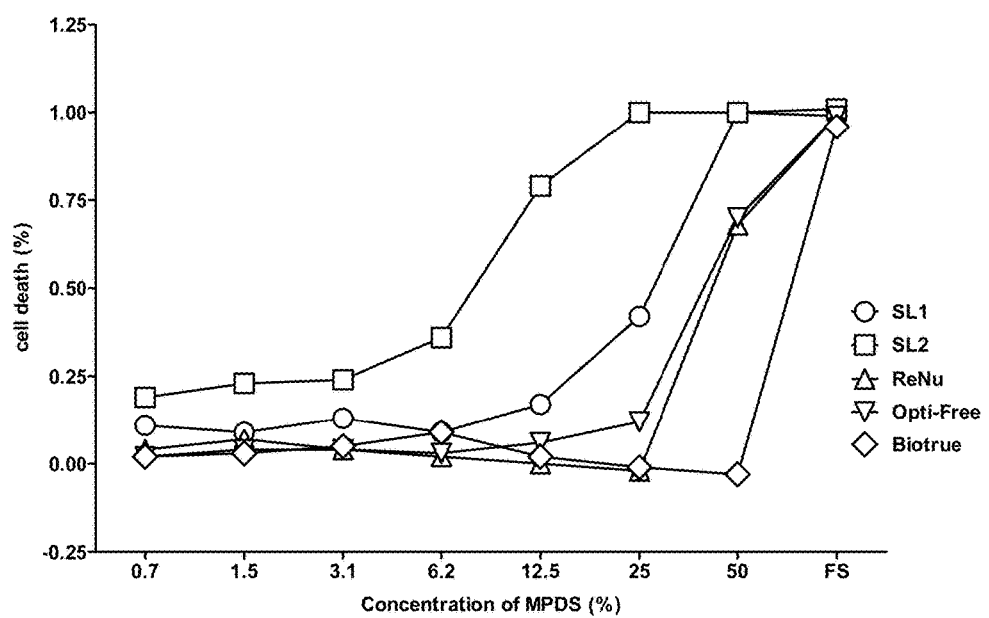
FIG. 2 shows cytotoxicity rankings of the two presently-disclosed multipurpose disinfection solutions (SOL01 and SOL02) and three commercially available multipurpose disinfection solutions: BioTrue (SOL05)<Opti-Free (SOL03)≤ReNu (SOL04)≤SOL01<SOL02.

The recent use of *Bacillus anthracis* as a bioterrorism agent has demonstrated the need for a solution that can effectively inactivate anthrax spores and that does not damage the surfaces to which it is applied, such as offices, computers, and surrounding equipment. In response to recent anthrax contamination scares, the U.S. Environmental Protection Agency has tested and recommended various disinfection products for use in emergency cleanup, including chlorine dioxide ($C10_2$). $C10_2$ was found to be effective only on hard surfaces at a concentration of 500 mg per liter with a 30-minute contact period. $C10_2$ blends have an approximate pH of 4 and may cause extensive damage to walls, computers, and other equipment to which they are applied.

Environmental hygiene beyond bioterrorism response is an area of growing concern. Exposure to biocontaminants, including certain molds, can lead to illnesses. Significant effort is required to achieve the necessary level of decontamination in the remediation of buildings, schools, and residences that are contaminated with mold.

Compositions that provide disinfection without damage to surfaces or tissue are necessary for proper cleaning and maintenance of contact lenses. There are over 40 million contact lens wearers in the United States, with more than 100 million estimated wearers worldwide. Regular use of contact lenses without proper hygienic maintenance may lead to multiple pathologies of the eye, including microbial keratitis. More than 80,000 eye infections occur per year in the US alone, with over 80% occurring in contact lens users. Approximately 1 in 600 contact lens users experience an infection requiring some medical intervention each year. Current commercial multipurpose disinfection solutions (MPDS) are developed for regular cleaning and antimicrobial disinfection to minimize the risks of potential adverse reactions associated with contact lens wear; however, currently-used solutions do not adequately disinfect or sterilize contact lenses, as evidenced by eye infection rates.

There are numerous other areas that may benefit from improved means of disinfection, including medical and paramedical device cleaning, dental instruments, medical appliances cleaning, high-level disinfectants and sterilants, and broad spectrum antimicrobial hygiene in the clinical environment.

MPDS are the most widely used cleaners and disinfectants worldwide. These products are typically composed of a single solution for disinfection and sterilization in various medical and environmental settings, yet this approach has proven to be infective. The majority of commercially-available MPDS currently use the same active ingredient disinfectant, organic salts of biguanide-based antimicrobials, at equivalent concentrations in their formulations, making it easier for these products to receive FDA approval at low cost. However, this provides limited disinfection across the microbial spectrum and increases the potential for unwanted microbial growth on surfaces.

Some MPDS contain an additional disinfecting agent, quaternary ammonium (Polyquad), at very low concentrations. Biguanides contain cationic active sites that facilitate cellular lysis through bacteria cell wall interaction, while the addition of an ammonium-based chemical increases the stress upon the diverse microbial constituents that a MPDS is required to kill and/or deactivate.

An optimized disinfecting solution would preferably have broad spectrum antimicrobial activity and relatively low cytotoxicity. The compositions and methods disclosed herein incorporate multiple chemical class microbial stressors to reduce microbial burden by direct killing and/or deactivation. Different ingredients are utilized for different groups of infective agents and pathogens, applying the concept of incorporating multiple stressors to achieve disinfection.

Detailed descriptions of one or more embodiments are provided herein. It is to be understood, however, that the present disclosure may be embodied in various forms. Therefore, specific details disclosed herein are not to be interpreted as limiting, but rather as a basis for the claims and as a representative basis for teaching one skilled in the art to employ the present disclosure in any appropriate manner.

Wherever the phrase "for example," "such as," "including" and the like are used herein, the phrase "and without limitation" is understood to follow unless explicitly stated otherwise. Similarly "an example," "exemplary" and the like are understood to be non-limiting.

The term "substantially" allows for deviations from the descriptor that don't negatively impact the intended purpose. Descriptive terms are understood to be modified by the term "substantially" even if the word "substantially" is not explicitly recited. Therefore, for example, the phrase "wherein the lever extends vertically" means "wherein the lever extends substantially vertically" so long as a precise vertical arrangement is not necessary for the lever to perform its function.

The terms "comprising" and "including" and "having" and "involving" (and similarly "comprises", "includes," "has," and "involves") and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a process involving steps a, b, and c" means that the process includes at least steps a, b, and c. Wherever the terms "a" or "an" are used, "one or more" is understood, unless such interpretation is nonsensical in context.

Some embodiments of the MPDS disclosed herein contain either three or four active disinfection components with disinfecting qualities and distinct mechanisms of action for microbial killing and/or deactivation. To achieve significant disinfection, up to and including sterilization, numerous types of microorganisms, such as bacteria, spore formers, fungi/yeasts, protozoa, helminths/helminth eggs, and viruses, spanning multiple Kingdoms are presumed to be encountered. Thus, a combination of chemicals selected for disinfection must possess multiple mechanisms of disinfection in order to completely disinfect and sterilize all possible components of contamination.

As used herein "stabilized chlorine dioxide" or "SCD" refers to an aqueous sodium chlorite ($NaClO_2$) solution. In some embodiments, stabilized chlorine dioxide is prepared by buffering sodium chlorite with a carbonate or a phosphate, and hydrogen peroxide. In addition to sodium chlorite, stabilized chlorine dioxide may further comprise sodium chlorate ($NaClO_3$) and sodium chloride (NaCl). In some embodiments and under the right pH condition stabilized chlorine dioxide may further comprise chlorine dioxide ($ClO_2$). In some embodiments, the composition described herein comprises stabilized chlorine dioxide as a source of sodium chlorite. In some embodiments, the stabilized chlorine dioxide is present in an amount ranging from about 0.005% to about 1.0% (w/w). In some embodiments, sodium chlorite is present in the composition in an amount ranging from about 0.0001% to about 0.1% (w/w). In some embodiments, the oxychlorine-based component of the composition described herein (e.g. sodium chlorite, stabilized chlorine dioxide, or chlorine dioxide) inhibits the cellular protein synthesis. In some embodiments, the oxychlorine-based component of the composition described herein (e.g. sodium chlorite, stabilized chlorine dioxide, or chlorine dioxide) inhibits the destruction of disulfide bonds.

As used herein "quaternary ammonium cations" also known as quats, refer to positively charged polyatomic ions of the structure $NR_4^+$, R being an alkyl group or an aryl group. Unlike the ammonium ion ($NH_4^+$) and the primary, secondary, or tertiary ammonium cations, the quaternary ammonium cations are permanently charged, independent of the pH of their solution. Quaternary ammonium salts or quaternary ammonium compounds are salts of quaternary ammonium cations. In some embodiments, the composition described herein comprises a quaternary ammonium salt. In some embodiments, the quaternary ammonium salt comprises a C12 or C14 alkyl chain. In some embodiments, the quaternary ammonium salt is not benzalkonium chloride. In some embodiments, the quaternary ammonium salt is C12-C14-alkyl(ethylbenzyl)dimethylammonium chloride. In some embodiments, the quaternary ammonium salt, e.g., C12-C14-alkyl(ethylbenzyl)dimethylammonium chloride is present in the composition in an amount ranging from about 0.00005% to about 0.1% (w/w), from about 0.001% to about 0.1% (w/w), or from about 0.001% to about 0.05% (w/w). In some embodiments, the quaternary ammonium salt destroys phospholipids within microbial cell wall, prompting autolysis, and microbial cell entry for the oxychlorine-based component in the formulation (e.g. sodium chlorite, stabilized chlorine dioxide, or chlorine dioxide).

As used herein "ammonium chloride" refers to $NH_4Cl$. In some embodiments, the composition described herein comprises ammonium chloride. In some embodiments, the ammonium chloride is present in the composition in an amount ranging from about 0.001% to about 2.0% (w/w). In some embodiments, ammonium chloride enhances the effectiveness for autolysis on hard-to-kill Gm-bacteria and spore formers, fungi, and recalcitrant organism such as pathogenic amoeba.

Compositions

Disclosed herein is a medical disinfecting composition comprising (a) a chlorite salt; (b) a quaternary ammonium salt; (c) ammonium chloride; and (d) water. In some embodiments, the water is deionized water. In some embodiments of a medical disinfecting composition, the chlorite salt is an alkali metal chlorite salt. In some embodiments of a medical disinfecting composition, the alkali metal chlorite salt is sodium chlorite. In some embodiments of a medical disinfecting composition, the sodium chlorite is present in an amount ranging from about 0.0001% to about 0.1% (w/w). In some embodiments of a medical disinfecting composition, sodium chlorite is present in the composition in an amount of about 0.0001%, about 0.0002%, about 0.0003%, about 0.0005%, about 0.0006%, about 0.0007%, about 0.0008%, about 0.0009%, about 0.001%, about 0.002%, about 0.003%, about 0.004%, about 0.005%, about 0.006%, about 0.007%, about 0.008%, about 0.009%, about 0.01%, about 0.02%, about 0.03%, about 0.04%, about 0.05%, about 0.06%, about 0.07%, about 0.08%, about 0.09%, or about 0.1% (w/w). In some embodiments of a medical disinfecting composition, the sodium chlorite is provided as a stabilized chlorine dioxide solution. In some embodiments of a medical disinfecting composition, the stabilized chlorine dioxide is present in an amount ranging from about 0.005% to about 1.0% (w/w). In some embodiments of a medical disinfecting composition, the stabilized chlorine dioxide is present in an amount of about 0.01%, about 0.02%, about 0.03%, about 0.04%, about 0.05%, about 0.06%, about 0.07%, about 0.08%, about 0.09%, about 0.10%, about 0.11%, about 0.12%, about 0.13%, about 0.14%, about 0.15%, about 0.16%, about 0.17%, about 0.18%, about 0.19%, about 0.2%, about 0.21%, about 0.22%, about 0.23%, about 0.24%, about 0.25%, about 0.30%, about 0.35%, about 0.40%, about 0.45%, about 0.50%, about 0.55%, about 0.60%, about 0.65%, about 0.70%, about 0.75%, about 0.80%, about 0.85%, about 0.90%, about 0.95%, or about 1.0% (w/w). In some embodiments of a medical disinfecting composition, the stabilized chlorine dioxide solution comprises chlorine dioxide. In some embodiments of a medical disinfecting composition, the quaternary ammonium salt comprises C12 or C14 alkyl chain. In some embodiments of a medical disinfecting composition, the quaternary ammonium salt is not benzalkonium chloride. In some embodiments of a medical disinfecting composition, the quaternary ammonium salt is C12-C14-alkyl(ethylbenzyl)dimethylammonium chloride. In some embodiments of a medical disinfecting composition, the C12-C14-alkyl(ethylbenzyl)dimethylammonium chloride is present in an amount ranging from about 0.00005% to about 0.1% (w/w). In some embodiments of a medical disinfecting composition, the C12-C14-alkyl(ethylbenzyl)dimethylammonium chloride is present in an amount ranging from about 0.001% to about 0.1% (w/w). In some embodiments of a medical disinfecting composition, the C12-C14-alkyl(ethylbenzyl)dimethylammonium chloride is present in the composition in an amount ranging from about 0.001% to about 0.1% (w/w), from about 0.001% to about 0.01% (w/w), or from about 0.001% to about 0.05% (w/w). In some embodiments of a medical disinfecting composition, the C12-C14-alkyl(ethylbenzyl)dimethylammonium chloride is present in the composition in an amount of about 0.0001%, about 0.001%, about 0.0015%, about 0.002%, about 0.0125%, about 0.025%, or about 0.05%. In some embodiments of a medical disinfecting composition, the ammonium chloride is present in an amount ranging from about 0.001% to about 2.0% (w/w). In some embodiments of a medical disinfecting composition, the ammonium chloride is present in the composition in an amount of about 0.001%, about 0.002%, about 0.003%, about 0.004%, about 0.005%, about 0.006%, about 0.007%, about 0.008%, about 0.009%, about 0.01%, about 0.02%, about 0.03%, about 0.04%, about 0.05%, about 0.06%, about 0.07%, about 0.08%, about 0.09%, about 0.10%, about 0.11%, about 0.12%, about 0.13%, about 0.14%, about 0.15%, about 0.16%, about 0.17%, about 0.18%, about 0.19%, about 0.2%, about 0.21%, about 0.22%, about 0.23%, about 0.24%, or about 0.25% (w/w). In some embodiments of a medical disinfecting composition, the composition further comprises a buffer to maintain the pH between about 7 and about 8. In some embodiments of a medical disinfecting composition, the pH is about 7. In some embodiments of a medical disinfecting composition, the buffer is a borate buffer. In some embodiments of a medical disinfecting composition, the buffer is a phosphate buffer.

In some embodiments of a medical disinfecting composition, the composition further comprises tonicity agents. Non-limiting example of tonicity agents are sodium chloride and potassium chloride. In some embodiments of a medical disinfecting composition, the tonicity agent is present in the composition in an amount of less than about 1% (w/w), or less than about 0.9%, or less than about 0.8%, or less than about 0.7%, or less than about 0.5%.

In some embodiments of a medical disinfecting composition, the composition further comprises a non-ionic surfactant. In some embodiments of a medical disinfecting composition, the non-ionic surfactant comprises a block copolymer. In some embodiments of a medical disinfecting composition, the block copolymer is Tetronic® 908. In some embodiments of a medical disinfecting composition, the non-ionic surfactant is present in the composition in an amount of less than about 1%, less than about 0.95%, less than about 0.9%, less than about 0.85%, less than about 0.8%, less than about 0.75%, less than about 0.7%, less than about 0.65%, less than about 0.6%, less than about 0.55%, less than about 0.5%, less than about 0.45%, less than about 0.4%, less than about 0.35%, less than about 0.3%, or less than about 0.25%.

Also disclosed herein is a medical disinfecting composition comprising (a) a predetermined concentration of chlorine dioxide; (b) a predetermined concentration of C12-C14-alkyl(ethylbenzyl)dimethylammonium chloride; (c) a predetermined concentration of ammonium chloride; and (d) an amount of deionized water sufficient to maintain the predetermined concentrations of chlorine dioxide, C12-C14-alkyl(ethylbenzyl)dimethylammonium chloride, and ammonium chloride. In some embodiments, the medical disinfecting composition further comprises an amount of stabilized water sufficient to maintain the predetermined concentrations of chlorine dioxide, C12-C14-Alkyl(ethylbenzyl)dimethylammonium chloride, and ammonium chloride. In some embodiments, the predetermined concentration of chlorine dioxide is between about 0.005% and about 1.0%. In some embodiments, the chlorine dioxide is provided as stabilized chlorine dioxide. In some embodiments, the predetermined concentration of C12-C14-Alkyl(ethylbenzyl)dimethylammonium chloride is between about 0.001% and about 0.1%.

In some embodiments, the predetermined concentration of ammonium chloride is between about 0.001% and about 2.0%. In some embodiments, the stabilized water is not corrosive or scaling. In some embodiments, the pH of the medical disinfecting composition is greater than or equal to about 8.0.

Also disclosed herein is a medical disinfecting composition comprising (a) a predetermined concentration of chlorine dioxide; (b) a predetermined concentration of C12-C14-alkyl(ethylbenzyl)dimethylammonium chloride; (c) a predetermined concentration of sodium nitrite; and (d) an amount of deionized water sufficient to maintain the predetermined concentrations of chlorine dioxide, C12-C14-alkyl(ethylbenzyl)dimethylammonium chloride, and sodium nitrite. In some embodiments, the medical disinfecting composition further comprises an amount of stabilized water sufficient to maintain the predetermined concentrations of chlorine dioxide, C12-C14-alkyl(ethylbenzyl)dimethylammonium chloride, and sodium nitrite. In some embodiments, the predetermined concentration of chlorine dioxide is between about 0.005% and about 1.0%. In some embodiments, the chlorine dioxide is provided as stabilized chlorine dioxide. In some embodiments, the predetermined concentration of C12-C14-alkyl(ethylbenzyl)dimethylammonium chloride is between about 0.001% and about 0.1%. In some embodiments, the predetermined concentration of sodium nitrite is between about 0.001% and about 2.0%. In some embodiments, the stabilized water is not corrosive or scaling. In some embodiments, the pH of the medical disinfecting composition is less than or equal to about 6.5.

Also disclosed herein is a medical disinfecting composition comprising (a) a predetermined concentration of peracetic acid (b) a predetermined concentration of C12-C14-alkyl(ethylbenzyl)dimethylammonium chloride; (c) a predetermined concentration of ammonium chloride; and (d) an amount of deionized water sufficient to maintain the predetermined concentrations of peracetic acid, C12-C14-alkyl(ethylbenzyl)dimethylammonium chloride, and ammonium chloride. In some embodiments, the medical disinfecting composition further comprises an amount of stabilized water sufficient to maintain the predetermined concentrations of peracetic acid, C12-C14-alkyl(ethylbenzyl)dimethylammonium chloride, and ammonium chloride. In some embodiments, the predetermined concentration of peracetic acid is between about 0.005% and about 1.0%. In some embodiments, the predetermined concentration of C12-C14-alkyl(ethylbenzyl)dimethylammonium chloride is between about 0.001% and about 0.1%. In some embodiments, the predetermined concentration of ammonium chloride is between about 0.001% and about 2.0%. In some embodiments, the stabilized water is not corrosive or scaling. In some embodiments, the pH of the medical disinfecting composition is greater than or equal to about 8.0.

Also disclosed herein is a medical disinfecting composition comprising (a) a predetermined concentration of peracetic acid; (b) a predetermined concentration of C12-C14-alkyl(ethylbenzyl)dimethylammonium chloride; (c) a predetermined concentration of sodium nitrite; and (d) an amount of deionized water sufficient to maintain the predetermined concentrations of peracetic acid, C12-C14-alkyl(ethylbenzyl)dimethylammonium chloride, and sodium nitrite. In some embodiments, the medical disinfecting composition further comprises an amount of stabilized water sufficient to maintain the predetermined concentrations of peracetic acid, C12-C14-alkyl(ethylbenzyl)dimethylammonium chloride, and sodium nitrite. In some embodiments, the predetermined concentration of peracetic acid is between about 0.005% and about 1.0%. In some embodiments, the predetermined concentration of C12-C14-alkyl(ethylbenzyl)dimethylammonium chloride is between about 0.001% and about 0.1%.

In some embodiments, the predetermined concentration of sodium nitrite is between about 0.001% and about 2.0%. In some embodiments, the stabilized water is not corrosive or scaling. In some embodiments, the pH of the composition is less than or equal to about 6.5.

In some embodiments, the predetermined concentration of chlorine dioxide comprises about 0.01%, the predetermined concentration of C12-C14-alkyl(ethylbenzyl)dimethylammonium chloride comprises about 0.002%, the predetermined concentration of ammonium chloride comprises about 0.1% to about 0.005%, and the chlorine dioxide is provided as stabilized chlorine dioxide. In some embodiments, the pH of the composition is between about 6.5 and about 11. In some embodiments, the oxidation-reduction potential (ORP) of the composition is between about −70 and about −90.

Also disclosed herein is a medical disinfecting composition comprising a predetermined concentration of chlorine dioxide; (a) a predetermined concentration of C12-C14-alkyl(ethylbenzyl)dimethylammonium chloride; (b) a predetermined concentration of ammonium chloride; (c) a predetermined concentration of peracetic acid; and (d) an amount of deionized water sufficient to maintain the predetermined concentrations of chlorine dioxide, C12-C14-alkyl(ethylbenzyl)dimethylammonium chloride, ammonium chloride, and peracetic acid. In some embodiments, the composition further comprises an amount of stabilized water sufficient to maintain the predetermined concentrations of chlorine dioxide, C12-C14-alkyl(ethylbenzyl)dimethylammonium chloride, ammonium chloride, and peracetic acid. In some embodiments, the predetermined concentration of chlorine dioxide is between about 0.005% and about 0.05%. In some embodiments, the predetermined concentration of C12-C14-alkyl(ethylbenzyl)dimethylammonium chloride is between about 0.001% and about 0.1%. In some embodiments, the predetermined concentration of ammonium chloride is between about 0.001% and about 0.1%. In some embodiments, the predetermined concentration of peracetic acid is between about 0.00005% and about 0.05%. In some embodiments, the stabilized water is not corrosive or scaling. In some embodiments, the chlorine dioxide is stabilized. In some embodiments, the pH of the composition is between about 2.0 and about 6.0. In some embodiments, the oxidation-reduction potential (ORP) comprises between about 170 and about 190. In some embodiments, the predetermined concentration of chlorine dioxide comprises about 0.01%, the predetermined concentration of C12-C14-alkyl(ethylbenzyl)dimethylammonium chloride comprises about 0.002%, the predetermined concentration of ammonium chloride comprises about 0.005%, the predetermined concentration of peracetic acid comprises about 0.0005%, and the chlorine dioxide is provided as stabilized chlorine dioxide.

In one embodiment, provided herein is a medical disinfecting composition comprising chlorine dioxide ("SCD"); C12-C14-Alkyl(ethylbenzyl)dimethylammonium chloride ("ADC"); ammonium chloride; and water. In an alternative embodiment, the aforementioned medical disinfecting composition comprises deionized water.

In one embodiment, the amount of chlorine dioxide is about 0.01% (w/w), the amount of C12-C14-alkyl(ethylbenzyl)dimethylammonium chloride is about 0.002% (w/w), the amount of ammonium chloride is about 0.1% to about 0.005% (w/w), and chlorine dioxide is provided as stabilized chlorine dioxide. In some embodiments, the pH of the composition is between about 6.5 and about 11, and the oxidation-reduction potential (ORP) of the composition is between about −70 and about −90. In some embodiments, the amount of chlorine dioxide is between about 0.005% and about 1.0% (w/w). In some embodiments, the chlorine dioxide is provided as stabilized chlorine dioxide. In some embodiments, the amount of C12-C14-alkyl(ethylbenzyl)dimethylammonium chloride is between about 0.001% and about 1.0% (w/w). In some embodiments, the amount of ammonium chloride is between about 0.001% and about 2.0% (w/w). The composition of the solution controls the alkalinity, hardness, pH, temperature, and total dissolved solids at an equilibrium or stable state. In some embodiments, the pH of the composition is greater than or equal to about 8.0. In some embodiments, the pH of the composition is greater than or equal to about 7.0. In some embodiments, the pH of the composition is about 7.0.

In another embodiment, provided herein is a medical disinfecting composition comprising chlorine dioxide; C12-C14-alkyl(ethylbenzyl)dimethylammonium chloride sodium nitrite; and water. In an alternative embodiment, the aforementioned medical disinfecting composition comprises deionized water. In some embodiments, the amount of chlorine dioxide is between about 0.005% and about 1.0% (w/w). In some embodiments, chlorine dioxide is provided as stabilized chlorine dioxide. In some embodiments, the amount of C12-C14-alkyl(ethylbenzyl)dimethylammonium chloride is between about 0.001% and about 0.1% (w/w). In some embodiments, the amount of sodium nitrite is between about 0.001% and about 2.0% (w/w). In some embodiments, the pH of the medical disinfecting composition is less than or equal to about 6.5.

In another embodiment, provide herein is medical disinfecting composition comprising peracetic acid; C12-C14-alkyl(ethylbenzyl)dimethylammonium chloride; ammonium chloride; and water. In some embodiments, the amount of peracetic acid is between about 0.005% and about 1.0% (w/w). In an alternative embodiment, the aforementioned medical disinfecting composition comprises deionized water. In some embodiments, the amount of C12-C14-alkyl (ethylbenzyl)dimethylammonium chloride is between about 0.001% and about 0.1% (w/w). In some embodiments, the amount of ammonium chloride is between about 0.001% and about 2.0% (w/w). In some embodiments, the pH of the medical disinfecting composition is greater than or equal to about 8.0.

In another embodiment, provided herein is a medical disinfecting composition comprising peracetic acid; C12-C14-alkyl(ethylbenzyl)dimethylammonium chloride sodium nitrite; and water. In some embodiments, the amount of peracetic acid is between about 0.005% and about 1.0% (w/w). In an alternative embodiment, the aforementioned medical disinfecting composition comprises deionized water. In some embodiments, the amount of C12-C14-alkyl (ethylbenzyl)dimethylammonium chloride is between about 0.001% and about 0.1% (w/w). In some embodiments, the amount of sodium nitrite is between about 0.001% and about 2.0% (w/w). In some embodiments, the pH of the composition is less than or equal to about 6.5.

In another embodiment, provided herein is a disinfecting composition comprising chlorine dioxide; C12-C14-alkyl (ethylbenzyl)dimethylammonium chloride; ammonium chloride; peracetic acid; and water. In an alternative embodiment, the aforementioned medical disinfecting composition comprises deionized water. In some embodiments, the amount of chlorine dioxide is between about 0.005% and about 0.05% (w/w). In some embodiments, the amount of C12-C14-alkyl(ethylbenzyl)dimethylammonium chloride is between about 0.001% and about 0.1% (w/w). In some embodiments, the amount of ammonium chloride is between about 0.001% and about 0.1% (w/w). In some embodiments, the amount of peracetic acid is between about 0.00005% and about 0.05% (w/w). In some embodiments, chlorine dioxide is provided as stabilized chlorine dioxide. In some embodiments, the pH of the medical disinfecting composition is between about 2.0 and about 6.0, and the oxidation-reduction potential (ORP) is between about 170 and about 190. In some embodiments, the amount of chlorine dioxide is about 0.01% (w/w), the amount of C12-C14-alkyl(ethylbenzyl)dimethylammonium chloride is about 0.002% (w/w), the amount of ammonium chloride is about 0.005% (w/w), the amount of peracetic acid is about 0.0005% (w/w), and chlorine dioxide is provided as stabilized chlorine dioxide. In other embodiments, the amount of chlorine dioxide is about 0.10% (w/w), the amount of C12-C14-alkyl(ethylbenzyl)dimethylammonium chloride is about 0.025% (w/w), the amount of peracetic acid is about 0.005% (w/w), the amount of ammonium chloride is about 0.05%, and chlorine dioxide is provided as stabilized chlorine dioxide. In some embodiments, the medical disinfecting composition has a pH approximately equal to 4 and an oxidation-reduction potential (ORP) equal to about 180.

In another embodiments, provided herein is a medical disinfecting composition with a pH approximately equal to 8, an oxidation-reduction potential (ORP) equal to about −81, and includes stabilized chlorine dioxide in an amount of about 0.10% (w/w), C12-C14-alkyl(ethylbenzyl)dimethylammonium chloride in an amount of about 0.025% (w/w), and ammonium chloride in an amount of about 0.05% (w/w).

Disinfecting Methods

Also disclosed herein is a method of disinfecting a medical device comprising contacting the medical device with a medical disinfecting composition comprising: (a) a chlorite salt; (b) a quaternary ammonium salt; (c) ammonium chloride; and (d) water. In some embodiments of a method of disinfecting a medical device, the chlorite salt is an alkali metal chlorite salt. In some embodiments of a method of disinfecting a medical device, the alkali metal chlorite salt is sodium chlorite. In some embodiments of a method of disinfecting a medical device, the sodium chlorite is present in an amount ranging from about 0.0001% to about 0.1% (w/w). In some embodiments of a method of disinfecting a medical device, the sodium chlorite is present in the composition in an amount of about 0.0001%, about 0.0002%, about 0.0003%, about 0.0005%, about 0.0006%, about 0.0007%, about 0.0008%, about 0.0009%, about 0.001%, about 0.002%, about 0.003%, about 0.004%, about 0.005%, about 0.006%, about 0.007%, about 0.008%, about 0.009%, about 0.01%, about 0.02%, about 0.03%, about 0.04%, about 0.05%, about 0.06%, about 0.07%, about 0.08%, about 0.09%, or about 0.1% (w/w). In some embodiments of a method of disinfecting a medical device, the sodium chlorite is provided as a stabilized chlorine dioxide solution. In some embodiments of a method of disinfecting a medical device, the stabilized chlorine dioxide is present in an amount ranging from about 0.005% to about 1.0% (w/w). In some embodiments of a method of disinfecting a medical device, the stabilized chlorine dioxide is present in an amount of about 0.01%, about 0.02%, about 0.03%, about 0.04%, about 0.05%, about 0.06%, about 0.07%, about 0.08%, about 0.09%, about 0.10%, about 0.11%, about 0.12%, about 0.13%, about 0.14%, about 0.15%, about 0.16%, about 0.17%, about 0.18%, about 0.19%, about 0.2%, about 0.21%, about 0.22%, about 0.23%, about 0.24%, about 0.25%, about 0.30%, about 0.35%, about 0.40%, about 0.45%, about 0.50%, about 0.55%, about 0.60%, about 0.65%, about 0.70%, about 0.75%, about 0.80%, about 0.85%, about 0.90%, about 0.95%, or about 1.0% (w/w). In some embodiments of a method of disinfecting a medical device, the stabilized chlorine dioxide solution comprises chlorine dioxide. In some embodiments of a method of disinfecting a medical device, the quaternary ammonium salt is not benzalkonium chloride. In some embodiments of a method of disinfecting a medical device, the quaternary ammonium salt is C12-C14-alkyl(ethylbenzyl)dimethylammonium chloride. In some embodiments of a method of disinfecting a medical device, the C12-C14-alkyl(ethylbenzyl)dimethylammonium chloride is present in an amount ranging from about 0.00005% to about 0.1% (w/w). In some embodiments of a method of disinfecting a medical device, the C12-C14-alkyl(ethylbenzyl)dimethylammonium chloride is present in an amount ranging from about 0.001% to about 0.1% (w/w). In some embodiments of a method of disinfecting a medical device, the C12-C14-alkyl(ethylbenzyl)dimethylammonium chloride is present in the composition in an amount ranging from about 0.001% to about 0.1% (w/w), from about 0.001% to about 0.01% (w/w), or from about 0.001% to about 0.05% (w/w). In some embodiments of a method of disinfecting a medical device, the C12-C14-alkyl(ethylbenzyl)dimethylammonium chloride is present in the composition in an amount of about 0.0001%, about 0.001%, about 0.0015%, about 0.002%, about 0.0125%, about 0.025%, or about 0.05%. In some embodiments of a method of disinfecting a medical device, the ammonium chloride is present in an amount ranging from about 0.001% to about 2.0% (w/w). In some embodiments of a method of disinfecting a medical device, the ammonium chloride is present in the composition in an amount of about 0.001%, about 0.002%, about 0.003%, about 0.004%, about 0.005%, about 0.006%, about 0.007%, about 0.008%, about 0.009%, about 0.01%, about 0.02%, about 0.03%, about 0.04%, about 0.05%, about 0.06%, about 0.07%, about 0.08%, about 0.09%, about 0.10%, about 0.11%, about 0.12%, about 0.13%, about 0.14%, about 0.15%, about 0.16%, about 0.17%, about 0.18%, about 0.19%, about 0.2%, about 0.21%, about 0.22%, about 0.23%, about 0.24%, or about 0.25% (w/w). In some embodiments of a method of disinfecting a medical device, the method further comprises a buffer to maintain the pH between about 7 and about 8. In some embodiments of a method of disinfecting a medical device, the pH is about 7. In some embodiments of a method of disinfecting a medical device, the medical device is in contact with a mammal tissue after contacting the medical device with a medical disinfecting composition. In some embodiments of a method of disinfecting a medical device, the mammal tissue is a human tissue. In some embodiments of a method of disinfecting a medical device, the medical device is selected from the group consisting of contact lenses, contact lens cases, surgical instruments, and dental instruments. In some embodiments, the medical disinfecting composition described herein is not used for water treatment purposes. In some embodiments, the medical disinfecting composition described herein is not used in pulp bleaching. In some embodiments, the medical disinfecting composition described herein is not used on non-medical devices.

Also disclosed herein is a method of disinfecting an object comprising (a) providing an amount of a disinfecting composition; (b) applying the amount of the disinfecting composition to the object to be disinfected; and (c) allowing the amount of the disinfecting composition applied to the object to contact the object for a predetermined amount of time.

In some embodiments, the disinfecting composition comprises (a) a predetermined concentration of chlorine dioxide; (b) a predetermined concentration of C12-C14-alkyl(ethylbenzyl)dimethylammonium chloride; (c) a predetermined concentration of ammonium chloride; (d) an amount of stabilized water sufficient to maintain the predetermined concentrations of chlorine dioxide, C12-C14-alkyl(ethylbenzyl)dimethylammonium chloride, and ammonium chloride; and (e) an amount of deionized water sufficient to maintain the predetermined concentrations of chlorine dioxide, C12-C14-alkyl(ethylbenzyl)dimethylammonium chloride, and ammonium chloride. In some embodiments, the predetermined concentration of chlorine dioxide is between about 0.005% and about 1.0%. In some embodiments, the chlorine dioxide is provided as stabilized chlorine dioxide. In some embodiments, the predetermined concentration of C12-C14-alkyl(ethylbenzyl)dimethylammonium chloride is between about 0.001% and about 0.1%.

In some embodiments of the disinfecting method, the predetermined concentration of ammonium chloride is between about 0.001% and about 2.0%. In some embodiments of the disinfecting method, the disinfecting composition comprises (a) a predetermined concentration of chlorine dioxide; (b) a predetermined concentration of C12-C14-alkyl(ethylbenzyl)dimethylammonium chloride; (c) a predetermined concentration of sodium nitrite; (d) an amount of stabilized water sufficient to maintain the predetermined concentrations of chlorine dioxide, C12-C14-alkyl(ethylbenzyl)dimethylammonium chloride, and sodium nitrite; and (e) an amount of deionized water sufficient to maintain the predetermined concentrations of chlorine dioxide, C12-C14-alkyl(ethylbenzyl)dimethylammonium chloride, and sodium nitrite. In some embodiments of the disinfecting method, the predetermined concentration of chlorine dioxide is between about 0.005% and about 1.0%. In some embodiments, the chlorine dioxide is provided as stabilized chlorine dioxide. In some embodiments of the disinfecting method, the predetermined concentration of C12-C14-alkyl(ethylbenzyl)dimethylammonium chloride is between about 0.001% and about 0.1%. In some embodiments of the disinfecting method, the predetermined concentration of sodium nitrite is between about 0.001% and about 2.0%. In some embodiments of the disinfecting method, the disinfecting composition comprises (a) a predetermined concentration of peracetic acid; (b) a predetermined concentration of C12-C14-alkyl(ethylbenzyl)dimethylammonium chloride; (c) a predetermined concentration of ammonium chloride; (d) an amount of stabilized water sufficient to maintain the predetermined concentrations of peracetic acid, C12-C14-alkyl(ethylbenzyl)dimethylammonium chloride, and ammonium chloride; and (e) an amount of deionized water sufficient to maintain the predetermined concentrations of peracetic acid, C12-C14-alkyl(ethylbenzyl)dimethylammonium chloride, and ammonium chloride. In some embodiments of the disinfecting method, the predetermined concentration of peracetic acid is between about 0.005% and about 1.0%. In some embodiments of the disinfecting method, the predetermined concentration of C12-C14-alkyl(ethylbenzyl)dimethylammonium chloride is between about 0.001% and about 0.1%. In some embodiments of the disinfecting method, the predetermined concentration of sodium nitrite is between about 0.001% and about 2.0%. In some embodiments of the disinfecting method, the disinfecting composition comprises (a) predetermined concentration of chlorine dioxide; (b) a predetermined concentration of C12-C14-alkyl(ethylbenzyl)dimethylammonium chloride; (c) a predetermined concentration of ammonium chloride; (d) a predetermined concentration of peracetic acid; (e) an amount of stabilized water sufficient to maintain the predetermined concentrations of chlorine dioxide, C12-C14-alkyl(ethylbenzyl)dimethylammonium chloride, ammonium chloride, and peracetic acid; and (f) an amount of deionized water sufficient to maintain the predetermined concentrations of chlorine dioxide, C12-C14-alkyl(ethylbenzyl)dimethylammonium chloride, ammonium chloride, and peracetic acid. In some embodiments of the disinfecting method, the predetermined concentration of chlorine dioxide is between about 0.005% and about 0.05%.

In some embodiments, the predetermined concentration of C12-C14-alkyl(ethylbenzyl)dimethylammonium chloride is between about 0.001% and about 0.1%. In some embodiments, the predetermined concentration of ammonium chloride is between about 0.001% and about 0.1%. In some embodiments of the disinfecting method, the predetermined concentration of peracetic acid is between about 0.00005% and about 0.05%. In some embodiments, the predetermined amount of time is between about two minutes and about four hours. In some embodiments of the disinfecting method, the predetermined amount of time is between about one minute and one hour.

In some embodiments, the method of disinfecting further comprises removing the amount of the disinfecting composition applied to the object from the object after the predetermined amount of time has passed. In some embodiments, the amount of disinfecting composition is removed from the object via one or more of the following methods: rinsing, drying, heat drying, wiping, sponging, blotting, rubbing, evaporation, or shaking. In some embodiments, the object is selected from the group comprising contact lenses, contact lens cases, medical devices, paramedical devices, and dental instruments.

In another embodiment, provided herein is a method of disinfecting a medical device comprising providing an amount of a disinfecting composition; applying the amount of the disinfecting composition to the medical device to be disinfected; and allowing the amount of the disinfecting composition applied to the medical device to contact the medical device for an amount of time. In some embodiments, the disinfecting composition comprises any one or more of the disinfecting composition disclosed herein, alone or in combination, or comprises any suitable disinfecting composition. In some embodiments, the amount of time is between about two minutes and about four hours. In other embodiments, the amount of time is between about one minute and one hour, or the amount of time is any amount of time that allows for a sufficient reduction in microbial or infectious agents.

In some embodiments, the method further comprises removing the amount of the disinfecting composition applied to the medical device from the medical device after the amount of time has passed. In some embodiments, the disinfection composition is removed from the medical device via one or more of the following methods: rinsing, drying, heat drying, wiping, sponging, blotting, rubbing, evaporation, shaking, or any other suitable removal method. In some embodiments, the medical device is selected from the group comprising contact lenses, contact lens cases, surgical instruments, and dental instruments.

Formulations disclosed herein utilize different ingredients to target, kill, and/or inactivate different groups of infective agents or pathogens, applying concepts for multi-stressing disinfection agents. Oxidizing disinfectant agents inactivate gram positive bacteria, viruses, and fungi. Quaternary amines inactivate gram negative bacteria. Ammonia, nitrous acid, or other appropriate non-charged disinfecting agents, depending upon the pH, may be included to inactivate parasites and protozoan oocysts. Surfactants enable the MPDS to be applied to various surfaces areas of a medical device.

EXPERIMENTAL SECTION

Example 1: Comparison of SOL01 and SOL02 Against Three Commercially-Available MPDS Standard methods for assessing the antimicrobial activity and the cytotoxicity of MPDS have been harmonized under International Standards Organization (ISO) standard laboratory procedures using a battery of preselected bacterial and fungal species. The standards for testing provide a standardized comparison among multiple MPDS. The use of standard laboratory procedures for testing provides an opportunity for benchmarking against a common battery of microbial challenge species.

Two presently-disclosed MPDS designated SOL01 (also referred to as "SL1") and SOL02 (also referred to as "SL2") were developed to be broadly effective against multiple microbial pathogens by inclusion of multiple chemical stressors rather than a single disinfection agent while simultaneously exerting minimal cytotoxicity upon tissues upon contact. The compositions of SOL01 and SOL02 are shown in the table of FIG. 1. The cytotoxicity and antimicrobial activity of SOL01 and SOL02 were compared against three commercially-available MPDS: ReNu fresh (active ingredient: Biguanide (0.0001%), Bausch & Lomb, Rochester, N.Y.), Opti-Free (active ingredients: Biguanide and Polyquad (polyquaternium; 0.001%), Alcon, Fort Worth, Tex.), and BioTrue (active ingredients: Biguanide (0.00013%), polyquaternium (0.0001%), and Hyaluronan (hyaluronic acid), Bausch & Lomb).

Relative antimicrobial disinfection and cytotoxicity of SOL01 and SOL02 and the three commercially-available MPDS were determined using ISO testing protocols 14729 (antimicrobial) and 10993 (cytotoxicity). The ISO-required battery of microorganisms (*S. aureus, P. aeruginosa, S. marcesens, C. albicans*, and *F. solani*) was used to assess the disinfection potential of each MPDS with contact times of one hour and four hours. Vero76 monkey kidney cells and XTT proliferation assay were used to assess in vitro cytotoxicity of each MPDS.

The disinfection potential of SOL01 and SOL02 in the ISO-specific antimicrobial assay demonstrated no bacterial or fungal plate growth for any of the microorganisms tested with as little as one hour contact time. All comparator MPDS, in contrast, showed significant growth at one hour contact times, with only slight reductions of bacterial or fungal growth after the four hours maximum contact time. Two of the three comparator MPDS exceeded 90% cell death at about 25% solution concentration dilution but required about 12% solution concentration dilution in order to minimize cytotoxicity from contact. SOL01 showed minimal cell death at approximately the same dilutions as comparator solutions, whereas SOL02 achieved similar performance with lower concentrations of about 1% to 3%.

The presently-disclosed MPDS (SOL01 and SOL02) combine broad spectrum antimicrobial killing against an array of microorganisms while maintaining minimal cytotoxicity on target tissues as demonstrated in vitro. The performance of SOL01 in the two ISO-recommended standard assays exceeded the three commercially-available comparator MPDS in antimicrobial activity, yet maintained a similar cytotoxicity profile. Optimization of SOL01 and SOL02 for maintaining hygiene of contact lenses and contact lens cases may reduce toxic effects while still maintaining effective prevention of ocular infections from microbial contamination.

Cytotoxicity

Figure 4:
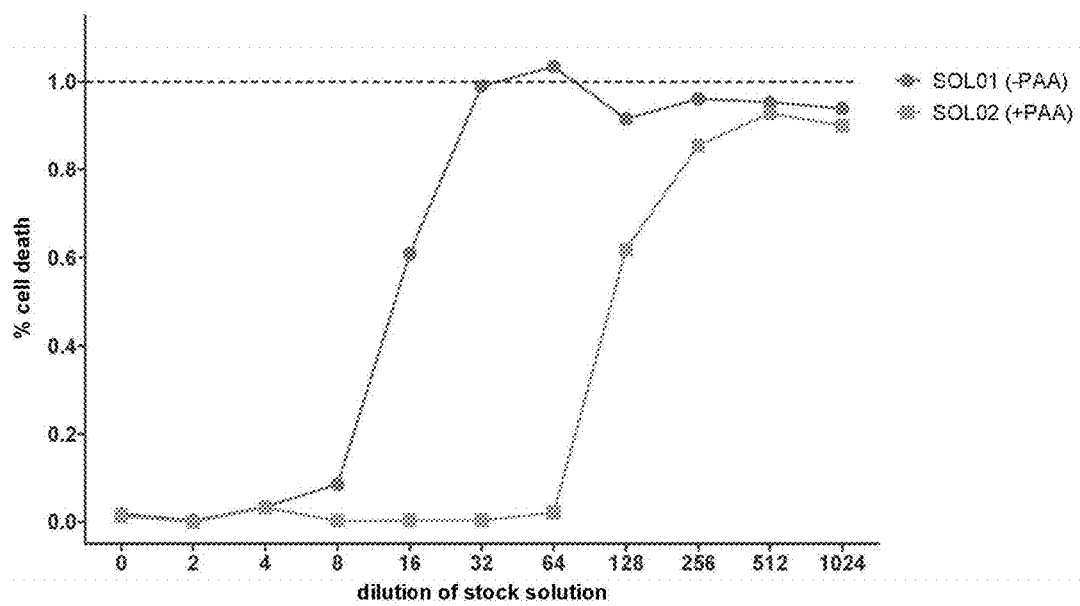
FIG. 4 shows the cytotoxic activity of the two presently-disclosed multipurpose disinfection solutions (SOL01 and SOL02).
Figure 5:
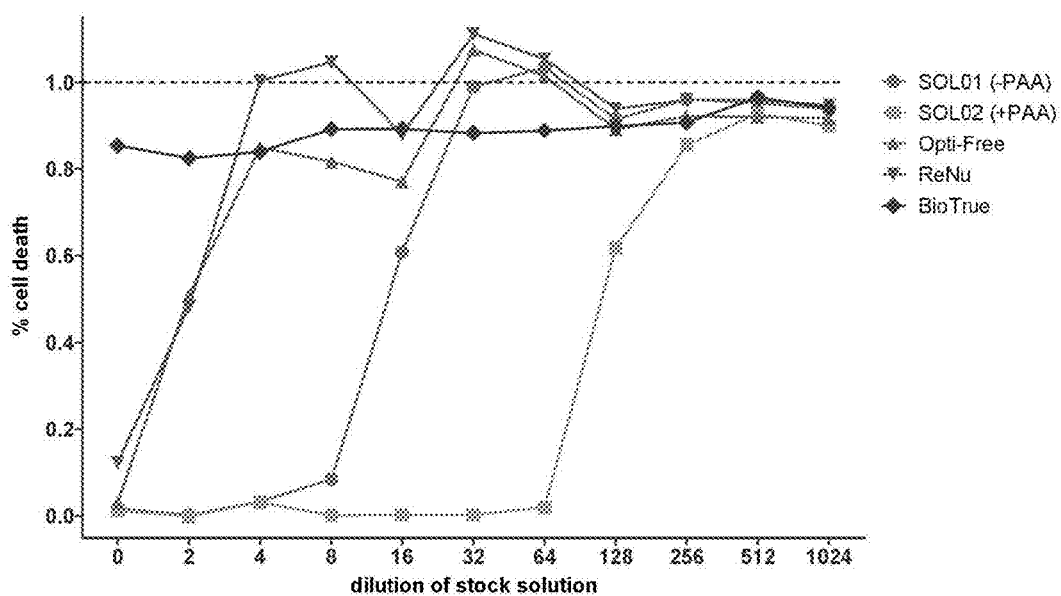
FIG. 5 shows a comparison of the two presently-disclosed multipurpose disinfection solutions (SOL01 and SOL02) and three commercially available multipurpose disinfection solutions (BioTrue (SOL05), Opti-Free (SOL03), and ReNu (SOL04)).

Cytotoxicity activity was evaluated in vitro based upon methods described in ISO standard 10993-5 (Biological Evaluation of Medical Devices—Part 5: Tests for in vitro cytotoxicity). A colony-formation assay was conducted using African Green Monkey kidney cells (Vero76), one cell line recommended for use under this testing regime. Approximately 1.0E+06 Vero76 cells in 2 mL of medium (minimum essential medium+5% fetal calf serum: Life Technologies, CA, USA) were inoculated into 6-well culture plates (Life Technologies, CA, USA) and cultured for about 48 hours at 37° C. at 5% $CO_2$ until adherent growth was confirmed. After washing and removal of the media, 1 mL of each SOL01, SOL02, and commercial MPDS was diluted with deionized sterile water and then added individually into individual wells at serial dilutions up to 1:512. Physiological saline was used as a negative control. Plates were incubated for about 48 hours at 37° C. at 5% $CO_2$ and then washed. Substrate was added and read at 490 nm. Proliferation was calculated in triplicate as (mean absorbance)×100/(mean absorbance/negative control group). As shown in FIG. 2, FIG. 4 and FIG. 5, results were plotted, and the relative cytotoxicity of each product compared.

All solutions were cytotoxic at full strength and showed a concentration-dependent increase in cytotoxicity as solution concentration increased. SOL02 was not cytotoxic at low concentrations of about 1% to about 3% but gradually increased to be highly cytotoxic at about 25%. ReNu, Opti-Free, and SOL01 were not cytotoxic at concentrations between about 25% and about 12.5% but increased two-fold in toxicity at about 50% concentration. BioTrue was not cytotoxic at about 50% solution concentration but was highly cytotoxic at full strength. Cytotoxicity rankings of the MPDS are as follows: BioTrue<Opti-Free≤ReNu≤SOL01<SOL02, as shown in FIG. 2.

Antimicrobial Activity

Antimicrobial activity was evaluated by using the methods described as a 'stand-alone' contact lens disinfection test (ISO 14729, 2001), which requires that the MPDS product must be capable of reducing the viability of specified bacterial and fungal species by three logs (99.9%) and one log (90%), respectively, within a particular timeframe. The standard bacterial and fungal organisms prescribed by the standard method are *Pseudomonas aeruginosa* IFO13275 (also referred to as "Pa"), *Staphylococcus aureus* IFO13276 (also referred to as "Sa"), *Serratia marcescens* ATCC13880 (also referred to as "Sm"), *Candida albicans* IFO1594 (also referred to as "Ca") and *Fusarium solani* ATCC36031 (also referred to as "Fs"). *P. aeruginosa*, *S. aureus* and *S. marcescens* were obtained commercially (ATCC, Manassas, Va.) as lyophilized packs. Bacterial cultures were reconstituted in soya broth and incubated for about 24 hours at 25° C. *C. albicans* and *F. solani* were obtained commercially (ATTC) and were grown in Sabouraud's dextrose in a similar fashion. All microorganisms were harvested using methods described in the ISO 14729 standard and adjusted for concentration through centrifugation and dilution with PBS. Final challenge concentrations of each approximated 1.0E+06 to 1.0E+07 CFU/ml.

A known volume (100 μl) of the microbial suspension was added to 9.9 mL of each MPDS in a polypropylene tube under sterile conditions. Mixtures were incubated at 25° C. for 1 hour, 2 hours, or 4 hours. After the prescribed contact time, the mixtures were sterile filtered through 0.45 μm analytical filter funnels (140-4045, Fisher Scientific) and washed twice with sterile DPBS. Each filter was aseptically removed from the filter funnel, laid upon one of TSA (*P. aeruginosa*, *S. aureus*), SDA (*S. marcescens*) or PDA (*C. albicans* and *F. solani*), and incubated at 25° C. for growth. Colonies were counted after about 48 hours of incubation. Each assay was performed in duplicate.

Figure 6:
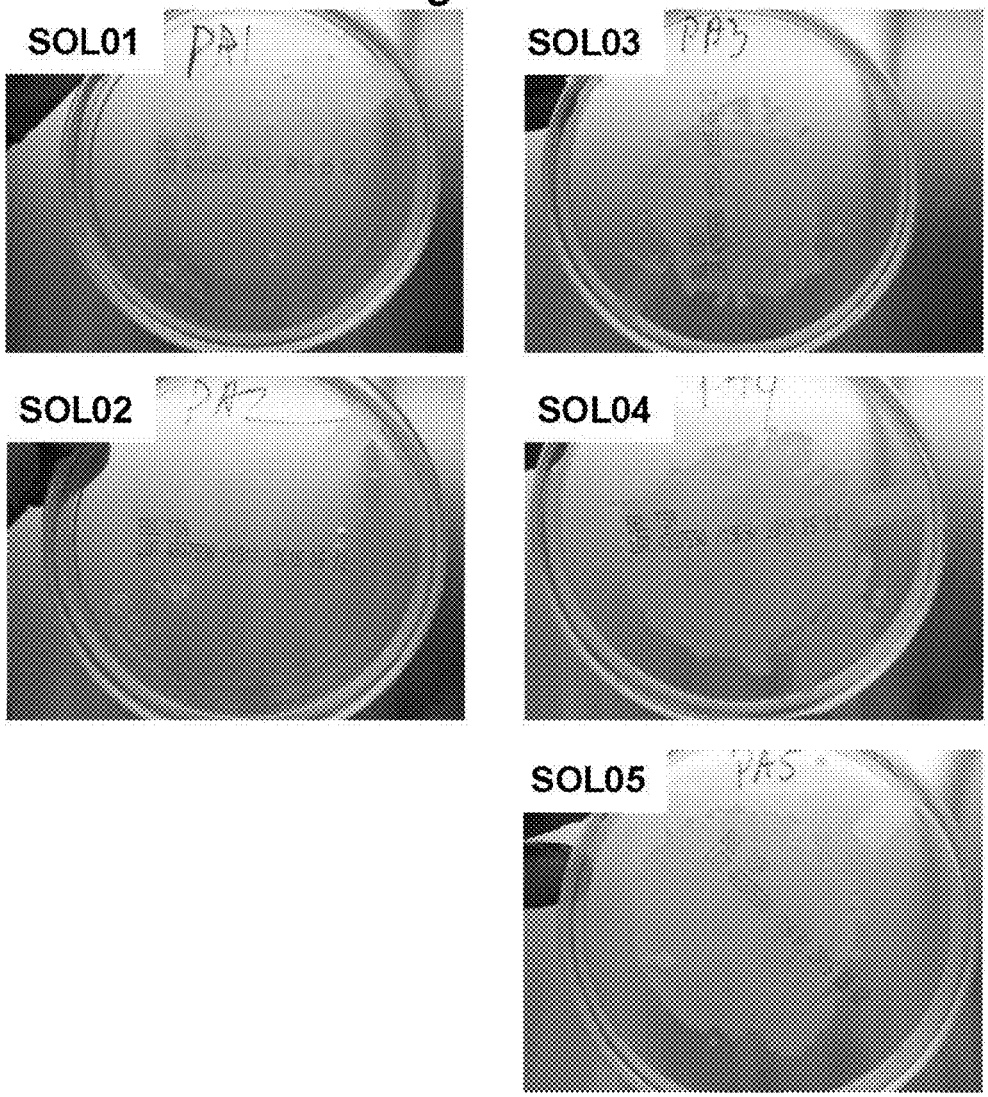
FIG. 6 shows the results of one hour of contact time with the two presently-disclosed multipurpose disinfection solutions (SOL01 and SOL02) and three commercially available multipurpose disinfection solutions (BioTrue (SOL05), Opti-Free (SOL03), and ReNu (SOL04)) for *P. aeruginosa* (ATCC 9027).
Figure 7:
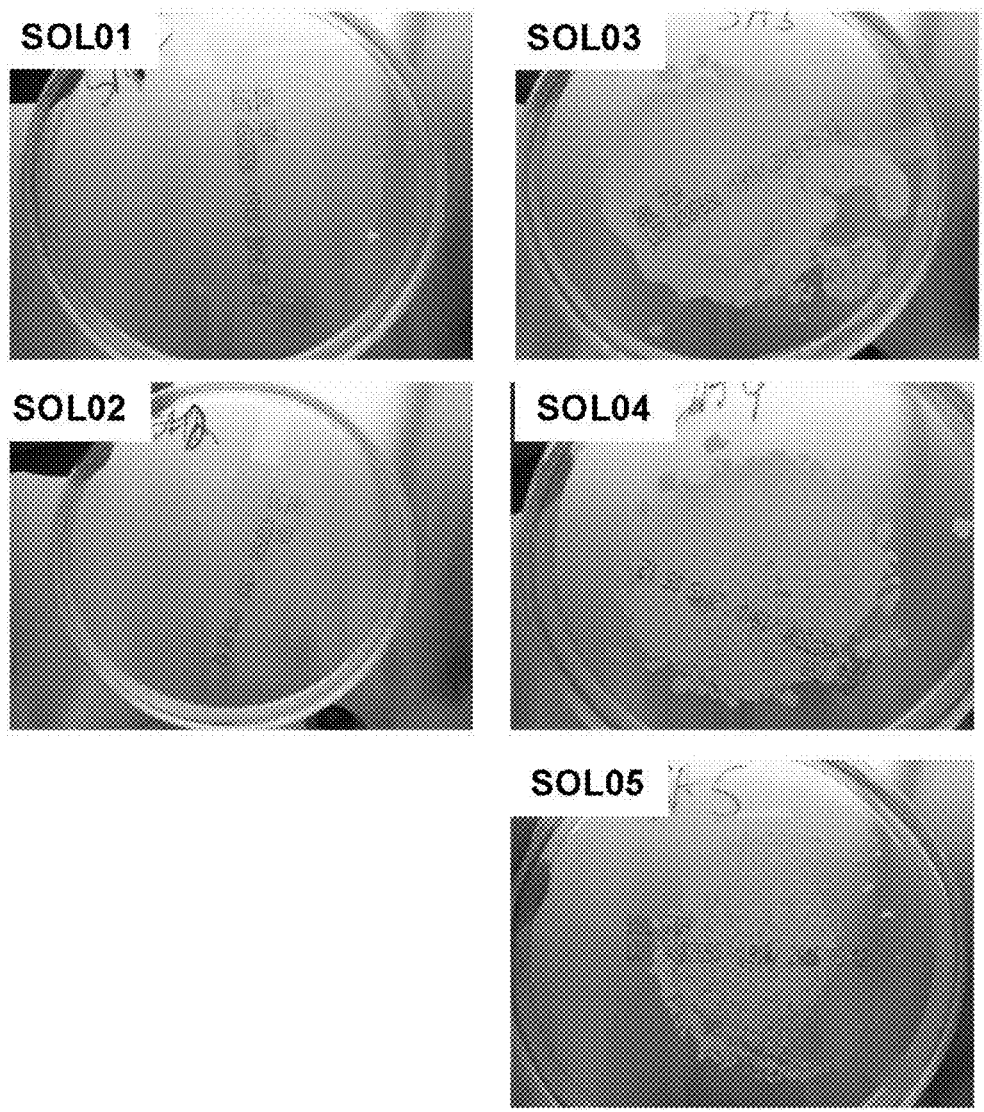
FIG. 7 shows the results of one hour of contact time with the two presently-disclosed multipurpose disinfection solutions (SOL01 and SOL02) and three commercially available multipurpose disinfection solutions (BioTrue (SOL05), Opti-Free (SOL03), and ReNu (SOL04)) for *S. aureus* (ATCC 6538).
Figure 8:
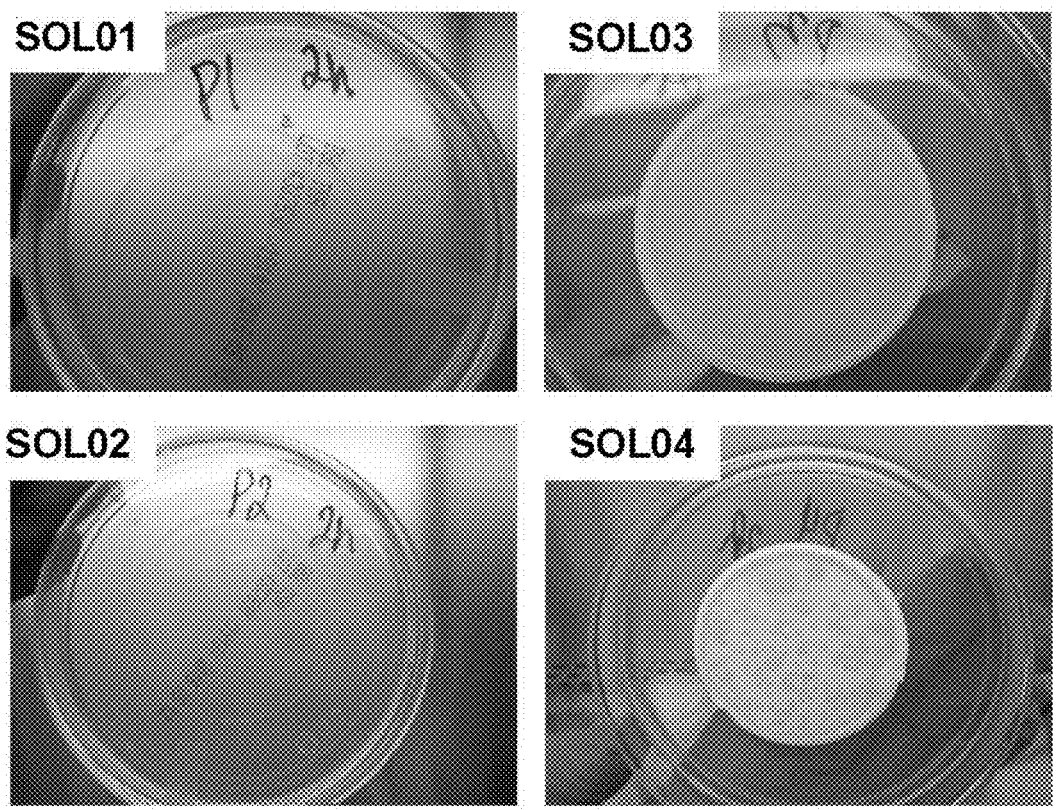
FIG. 8 shows the results of two hours of contact time with the two presently-disclosed multipurpose disinfection solutions (SOL01 and SOL02) and two commercially available multipurpose disinfection solutions (BioTrue (SOL05), Opti-Free (SOL03), and ReNu (SOL04)) for *P. aeruginosa* (ATCC 9027).
Figure 9:
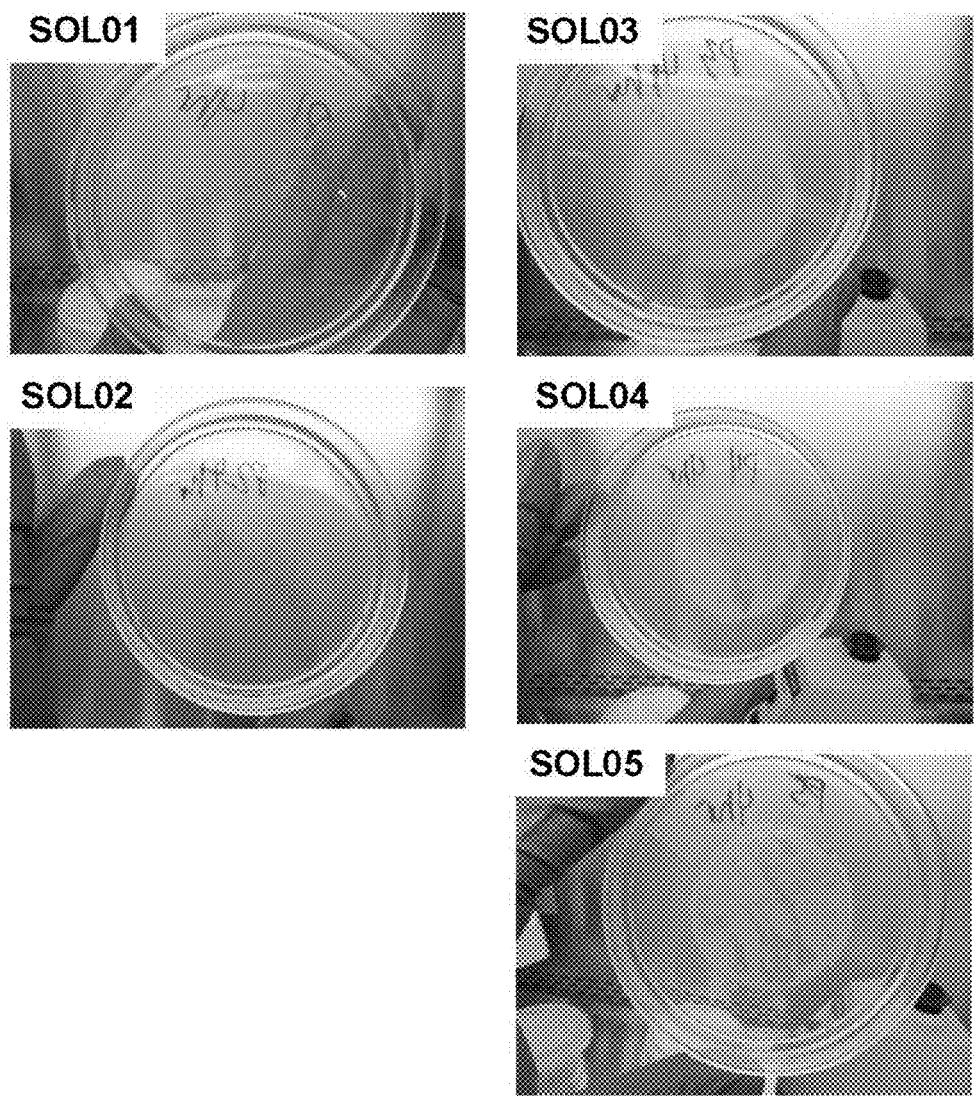
FIG. 9 shows the results of four hours of contact time the two presently-disclosed multipurpose disinfection solutions (SOL01 and SOL02) and three commercially available multipurpose disinfection solutions (BioTrue (SOL05), Opti-Free (SOL03), and ReNu (SOL04)) for *P. aeruginosa* (ATCC 9027).
Figure 10:
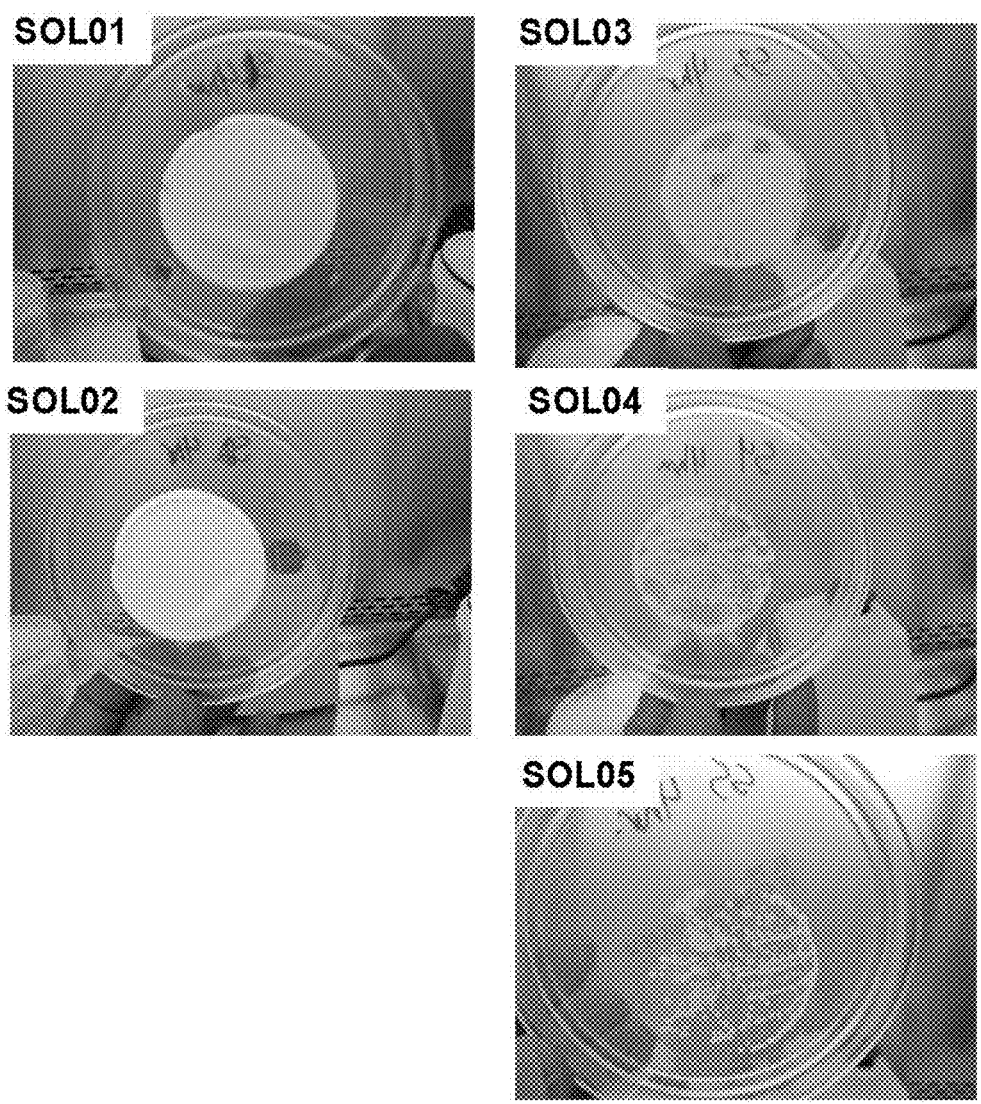
FIG. 10 shows the results of four hours of contact time with the two presently-disclosed multipurpose disinfection solutions (SOL01 and SOL02) and three commercially available multipurpose disinfection solutions (BioTrue (SOL05), Opti-Free (SOL03), and ReNu (SOL04)) for *S. aureus* (ATCC 6538).
Figure 11:
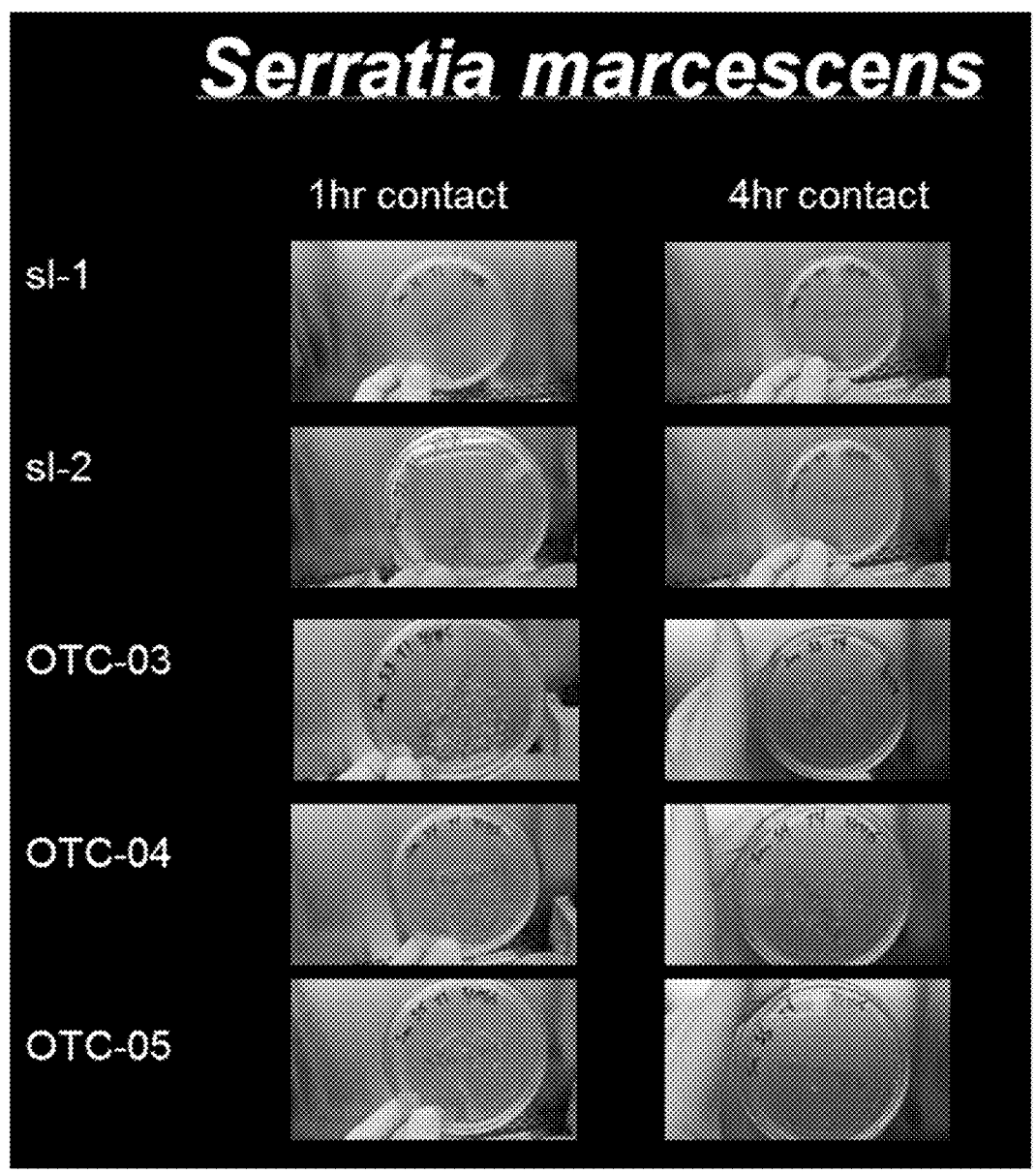
FIG. 11 shows the results of one hour and four hours of contact time with two presently-disclosed multipurpose disinfection solutions (SOL01 and SOL02) and three commercially available multipurpose disinfection solutions (BioTrue (SOL05), Opti-Free (SOL03), and ReNu (SOL04)) for *S. marcescens*.
Figure 12:
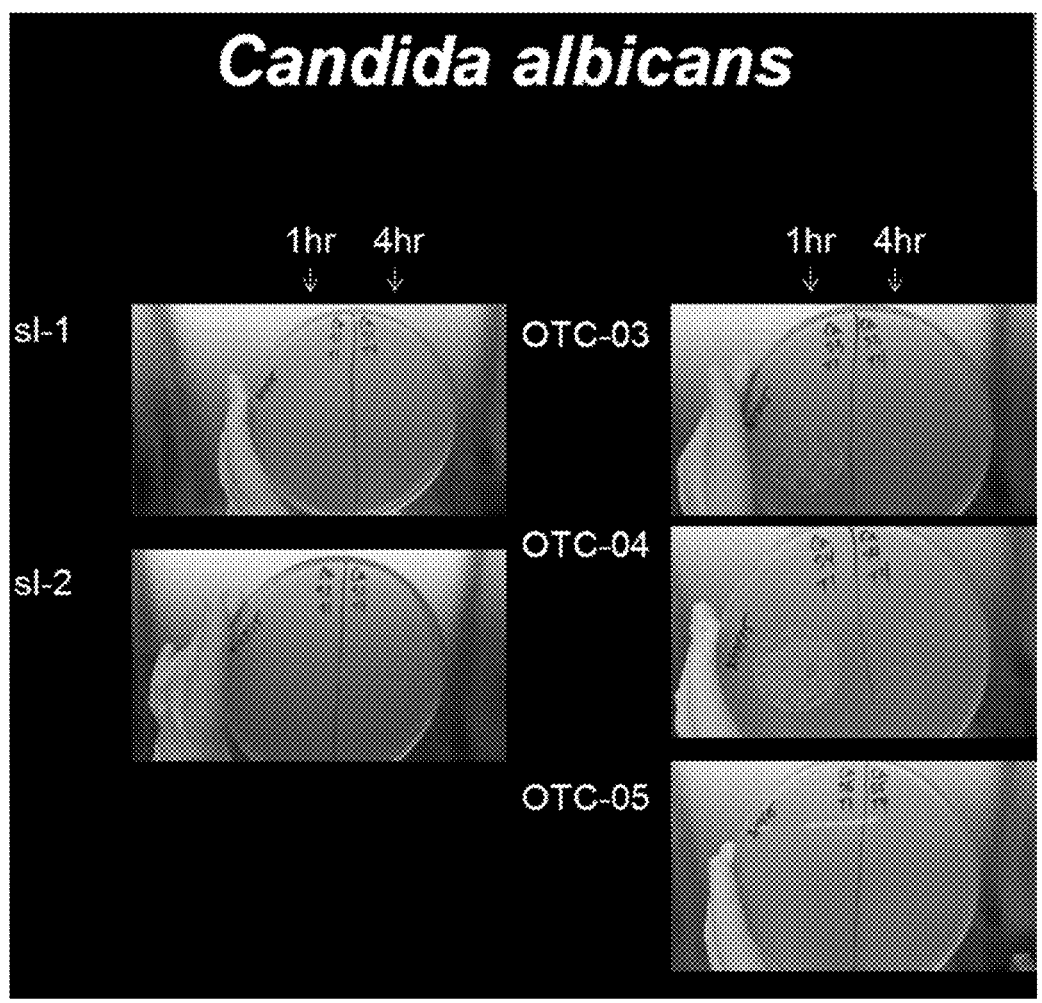
FIG. 12 shows the results of one hour and four hours of contact time with two presently-disclosed multipurpose disinfection solutions (SOL01 and SOL02) and three commercially available multipurpose disinfection solutions (BioTrue (SOL05), Opti-Free (SOL03), and ReNu (SOL04)) for *C. albicans*.
Figure 13:
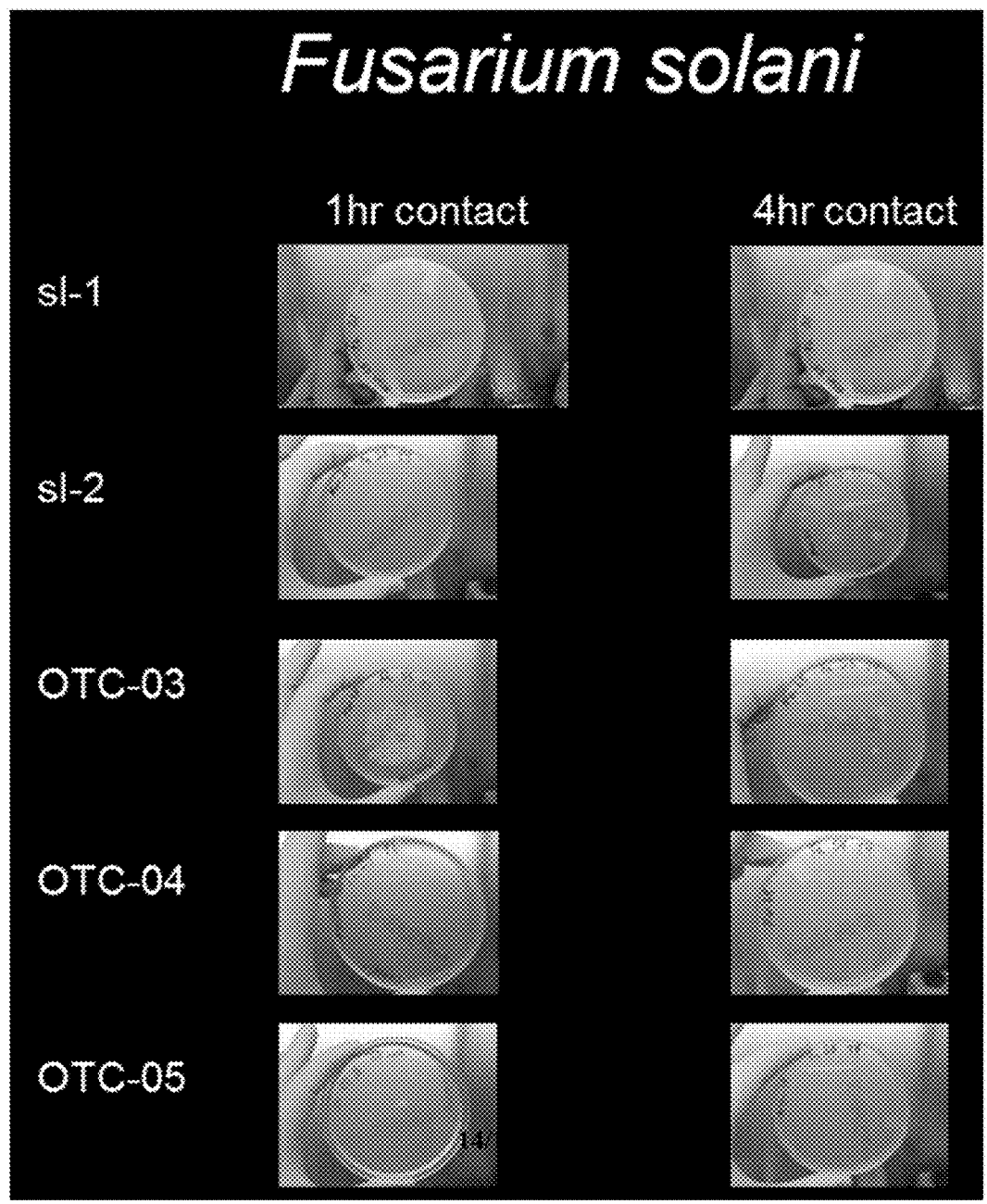
FIG. 13 shows the results of one hour and four hours of contact time with two presently-disclosed multipurpose disinfection solutions (SOL01 and SOL02) and three commercially available multipurpose disinfection solutions (BioTrue (SOL05), Opti-Free (SOL03), and ReNu (SOL04)) for *F. solani*.

Both SOL01 and SOL02 were completely sterilizing against all of the microorganisms tested. As summarized in FIG. 3 and depicted in FIG. 6-10, no growth on any of the plates at either the one hour or four hour contact time point was observed. In contrast, none of the three commercially available MPDS tested were effective in achieving any log reduction against *P. aeruginosa* (see FIG. 6, FIG. 8 and FIG. 9) or *S. aureus* (see FIG. 7 and FIG. 10) at either the one hour or four hour contact time point. Two of the three commercial solutions (ReNu and BioTrue) showed some effectiveness against *S. marcescens* at one hour of contact time, with all three solutions achieving adequate microbial reduction at four hours of contact time (see FIG. 3 and FIG. 11). Only one of the three commercial solutions (BioTrue) was effective against *C. albicans* at one hour of contact time, with all three requiring four hours of contact time to achieve some microbial reduction (see FIG. 3 and FIG. 12). All three commercial solutions showed some effectiveness against *F. solani* at one hour and four hour contact times (see FIG. 3 and FIG. 13). Two of the three commercial solutions (Opti-free and BioTrue) performed similarly to SOL01 and SOL02 at the four hour contact time against *F. solani*, indicating no growth of the fungi (see FIG. 3 and FIG. 12).

Both SOL01 and SOL02 were comprised primarily of stabilized chlorine dioxide. In addition to the chlorine-based disinfectant, a quaternary ammonium salt was included, which was shown to increase disinfection qualities. Ammonium chloride was added to increase the available ammonium ions in conjunction with the quaternary ammonium salt. Peracetic acid was added to SOL02, which subsequently lowered the pH to 5.5, possibly accounting for the increase in cytotoxicity in this particular formulation. The cytotoxicity testing for SOL01 indicated a toxicity profile within an acceptable range and highly comparable to the three commercially-available MPDS. Addition of components to isotonically balance the solution in combination with appropriate buffering and wetting agents may reduce the toxicity that was observed at concentrations over about 25%.

The combination of the three active ingredients in SOL01 resulted in a completely sterilizing action against all of the challenge organisms with as little as one hour contact time. These results are in stark contrast to the performance of the three commercially-available MPDS, which showed little ability to disinfect against standard microbial organisms using contact times of either one hour or four hours. Performance of the commercial MPDS against the two strains of gram negative bacteria (*P. aeruginosa* and *S. Marcescens*) and the one strain of gram positive bacteria (*S. aureus*) was unexpected, as log reductions of these organisms have been achieved in past studies with the same MPDS. Disinfection qualities of the commercial MPDS against the selected fungi, *C. albicans* and *F. solani*, were more in line with expectations based upon previous work showing marginal or poor performance. Each of SOL01 and SOL02 in contrast was completely sterilizing against both of the fungal organisms after only one hour of contact time.

The data shown here demonstrate that MPDS with multiple chemically-distinct active ingredients may be used as a disinfectant for a variety of applications. The MPDS disclosed herein surpass the current standard of care, represented by the commercially-available MPDS, in terms of both disinfection capability and cytotoxicity. These results establish that the multiple stressor approach disclosed herein is far superior for quick-acting disinfection across a broad spectrum of microorganisms when compared to commercial counterparts.

Example 2: Exemplary BBS Based Formulation with Biocidal Test Results

| Ingredient | A-2 % (W/W) | B-2 % (W/W) | C-2 % (W/W) | D-2 % (W/W) | E-2 % (W/W) | F-2 % (W/W) |
|---|---|---|---|---|---|---|
| Boric Acid | 0.850 | 0.850 | 0.850 | 0.850 | 0.850 | 0.850 |
| Sodium Borate | 0.130 | 0.130 | 0.130 | 0.130 | 0.130 | 0.130 |
| Sodium Chloride | 0.250 | 0.250 | 0.250 | 0.250 | 0.250 | 0.250 |
| Potassium Chloride | 0.250 | 0.250 | 0.250 | 0.250 | 0.250 | 0.250 |
| Tetronic 908 | 0.250 | 0.250 | 0.250 | 0.250 | 0.250 | 0.250 |
| Ammonium Chloride | — | — | — | 0.200 | 0.100 | 0.050 |
| Stabilized Chlorine Dioxide | 0.04 | 0.02 | 0.01 | — | — | — |
| pH | 7.39/7.44 | 7.39/7.44 | 7.39/7.44 | 7.39/7.44 | 7.39/7.44 | 7.39/7.44 |
| Osmolarity | 290 | 290 | 290 | 290 | 290 | 290 |
| Biocidal Test Results | | | | | | |
| *Staphylococcus aureus* | NG | NG | NG | Positive | Positive | Positive |
| *Pseadomonas aeruginosa* | NG | NG | NG | Positive | Positive | Positive |
| *Candida albicans* | NG | NG | Positive | Positive | Positive | Positive |
| *Fusarium solani* | Positive | Positive | Positive | Positive | Positive | Positive |

NG: no growth
Positive: at least 1 colony forming unit (CFU) of growth.

Example 3: Exemplary Phosphate Buffer Based Formulation with Biocidal Test Results

| Ingredient | A-3 % (W/W) | B-3 % (W/W) | C-3 % (W/W) | D-3 % (W/W) | E-3 % (W/W) | F-3 % (W/W) |
|---|---|---|---|---|---|---|
| Sodium Phosphate, Heptahydrate, Dibasic | 0.165 | 0.165 | 0.165 | 0.165 | 0.165 | 0.165 |
| Sodium Phosphate, Monohydrate, monobasic | 0.050 | 0.050 | 0.050 | 0.050 | 0.050 | 0.050 |
| Sodium Chloride | 0.650 | 0.650 | 0.650 | 0.650 | 0.650 | 0.650 |
| Potassium Chloride | 0.250 | 0.250 | 0.250 | 0.250 | 0.250 | 0.250 |
| Tetronic 908 | 0.250 | 0.250 | 0.250 | 0.250 | 0.250 | 0.250 |
| Ammonium Chloride | — | — | — | 0.200 | 0.100 | 0.050 |
| Stabilized Chlorine Dioxide | 0.04 | 0.02 | 0.01 | — | — | — |
| pH | 7.0 | 7.0 | 7.0 | 7.0 | 7.0 | 7.0 |
| Osmolarity | 290 | 290 | 290 | 290 | 290 | 290 |
| Biocidal Test Results | | | | | | |
| *Staphylococcus aureus* | NG | NG | NG | Positive | Positive | Positive |
| *Pseudomonas aeruginosa* | NG | NG | NG | Positive | Positive | Positive |
| *Candida albicans* | NG | NG | Positive | Positive | Positive | Positive |
| *Fusarium solani* | Positive | Positive | Positive | Positive | Positive | Positive |

NG: no growth
Positive: at least 1 colony forming unit (CFU) of growth.

Example 4: Exemplary Phosphate Buffer Based Formulation with Biocidal Test Results

| Ingredient | A-4 % (W/W) | B-4 % (W/W) | C-4 % (W/W) | D-4 % (W/W) | E-4 % (W/W) | F-4 % (W/W) |
|---|---|---|---|---|---|---|
| Sodium Phosphate, Heptahydrate, Dibasic | 0.165 | 0.165 | 0.165 | 0.165 | 0.165 | 0.165 |
| Sodium Phosphate, Monohydrate, monobasic | 0.050 | 0.050 | 0.050 | 0.050 | 0.050 | 0.050 |
| Sodium Chloride | 0.650 | 0.650 | 0.650 | 0.650 | 0.650 | 0.650 |
| Potassium Chloride | 0.250 | 0.250 | 0.250 | 0.250 | 0.250 | 0.250 |
| Tetronic 908 | 0.250 | 0.250 | 0.250 | 0.250 | 0.250 | 0.250 |

-continued

| Ingredient | A-4 % (W/W) | B-4 % (W/W) | C-4 % (W/W) | D-4 % (W/W) | E-4 % (W/W) | F-4 % (W/W) |
|---|---|---|---|---|---|---|
| Ammonium Chloride | — | 0.200 | 0.200 | — | — | — |
| Stabilized Chlorine Dioxide | 0.01 | 0.01 | — | — | — | — |
| C12-C14-alkyl(ethylbenzyl)dimethylammonium chloride (80%) | — | — | — | 0.050 | 0.025 | 0.0125 |
| pH | 7.0 | 7.0 | 7.0 | 7.0 | 7.0 | 7.0 |
| Osmolarity | 290 | 290 | 290 | 290 | 290 | 290 |
| Biocidal Test Results | | | | | | |
| *Staphylococcus aureus* | NG | NG | Positive | NG | NG | NG |
| *Pseudomonas aeruginosa* | NG | NG | Positive | NG | NG | NG |
| *Candida albicans* | Positive | NG | Positive | NG | NG | NG |
| *Fusarium solani* | Positive | Positive | Positive | NG | NG | NG |

NG: no growth
Positive: at least 1 colony forming unit (CFU) of growth.

Example 5: Exemplary Phosphate Buffer Based Formulation with Biocidal Test Results

| Ingredient | A-5 % (W/W) | B-5 % (W/W) | C-5 % (W/W) | D-5 % (W/W) | E-5 % (W/W) | F-5 % (W/W) | G-5 % (W/W) |
|---|---|---|---|---|---|---|---|
| Sodium Phosphate, Heptahydrate, Dibasic | 0.165 | 0.165 | 0.165 | 0.165 | 0.165 | 0.165 | 0.165 |
| Sodium Phosphate, Monohydrate, monobasic | 0.050 | 0.050 | 0.050 | 0.050 | 0.050 | 0.050 | 0.050 |
| Sodium Chloride | 0.650 | 0.650 | 0.650 | 0.650 | 0.650 | 0.650 | 0.650 |
| Potassium Chloride | 0.250 | 0.250 | 0.250 | 0.250 | 0.250 | 0.250 | 0.250 |
| Tetronic 908 | 0.250 | 0.250 | 0.250 | 0.250 | 0.250 | 0.250 | 0.250 |
| Ammonium Chloride | — | — | 0.20 | — | 0.20 | 0.20 | 0.20 |
| Stabilized Chlorine Dioxide | — | 0.01 | — | 0.01 | — | 0.01 | 0.01 |
| C12-C14-alkyl(ethylbenzyl)dimethylammonium chloride (80%) | 0.0125 | — | — | 0.0125 | 0.0125 | — | 0.125 |
| pH | 7.0 | 7.0 | 7.0 | 7.0 | 7.0 | 7.0 | 7.0 |
| Osmolarity | 290 | 290 | 290 | 290 | 290 | 290 | 290 |
| Biocidal Test Results | | | | | | | |
| *Staphylococcus aureus* | NG | NG | Positive | NG | NG | Positive | NG |
| *Pseadomonas aeruginosa* | Positive | Positive | Positive | NG | NG | NG | NG |
| *Candida albicans* | NG | Positive | Positive | NG | NG | Positive | NG |
| *Fusarium solani* | NG | Positive | Positive | NG | NG | Positive | NG |

NG: no growth
Positive: at least 1 colony forming unit (CFU) of growth.

Example 6: Exemplary Phosphate Buffer Based Formulation with Biocidal Test Results

| Ingredient | A-6 % (W/W) | B-6 % (W/W) | C-6 % (W/W) | D-6 % (W/W) | E-6 % (W/W) | F-6 % (W/W) | G-6 % (W/W) |
|---|---|---|---|---|---|---|---|
| Sodium Phosphate, Heptahydrate, Dibasic | 0.165 | 0.165 | 0.165 | 0.165 | 0.165 | 0.165 | 0.165 |
| Sodium Phosphate, Monohydrate, monobasic | 0.050 | 0.050 | 0.050 | 0.050 | 0.050 | 0.050 | 0.050 |

-continued

| Ingredient | A-6 % (W/W) | B-6 % (W/W) | C-6 % (W/W) | D-6 % (W/W) | E-6 % (W/W) | F-6 % (W/W) | G-6 % (W/W) |
|---|---|---|---|---|---|---|---|
| Sodium Chloride | 0.650 | 0.650 | 0.650 | 0.650 | 0.650 | 0.650 | 0.650 |
| Potassium Chloride | 0.250 | 0.250 | 0.250 | 0.250 | 0.250 | 0.250 | 0.250 |
| Tetronic 908 | 0.250 | 0.250 | 0.250 | 0.250 | 0.250 | 0.250 | 0.250 |
| Ammonium Chloride | 0.20 | 0.20 | 0.20 | 0.20 | 0.20 | — | — |
| Stabilized Chlorine Dioxide | 0.01 | 0.01 | 0.01 | 0.01 | 0.01 | — | — |
| C12-C14-alkyl(ethylbenzyl)dimethylammonium chloride (80%) | 0.0125 | 0.0075 | 0.0030 | 0.0010 | 0.0001 | 0.0075 | 0.0030 |
| pH | 7.0 | 7.0 | 7.0 | 7.0 | 7.0 | 7.0 | 7.0 |
| Osmolarity | 290 | 290 | 290 | 290 | 290 | 290 | 290 |
| Biocidal Test Results | | | | | | | |
| *Staphylococcus aureus* | NG | NG | NG | NG | NG | NG | NG |
| *Pseudomonas aeruginosa* | NG | NG | NG | NG | NG | NG | NG |
| *Candida albicans* | NG | NG | NG | NG | NG | NG | NG |
| *Fusarium solani* | NG | NG | NG | NG | Positive | NG | NG |

NG: no growth
Positive: at least 1 colony forming unit (CFU) of growth.

Example 7: Exemplary Phosphate/Borate Buffer Based Formulation with Biocidal Test Results

| Ingredient | A-7 % (W/W) | B-7 % (W/W) | C-7 % (W/W) | D-7 % (W/W) | E-7 % (W/W) | F-7 % (W/W) | G-7 % (W/W) | H-7 % (W/W) |
|---|---|---|---|---|---|---|---|---|
| Buffer | Borate | | | | Phosphate | | | |
| Stabilized Chlorine Dioxide | 0.005% to 1.0% | | | 0.005% to 1.0% | 0.005% to 1.0% | | | 0.005% to 1.0% |
| ammonium chloride | | 0.001% to 2.0% | | 0.001% to 2.0% | | 0.001% to 2.0% | | 0.001% to 2.0% |
| C12-14-alkyl(ethylbenzyl)dimethylammonium chloride (80%) | | | 0.00005% to 0.1% | 0.00005% to 0.1% | | | 0.00005% to 0.1% | 0.00005% to 0.1% |
| Biocidal Test Results | | | | | | | | |
| *P. aeruginosa* | NG | Positive | Positive | NG | NG | Positive | Positive | NG |
| *S. aureus* | NG | Positive | Positive | NG | NG | Positive | Positive | NG |
| *C. albicans* | Positive | Positive | NG | NG | Positive | Positive | NG | NG |
| *F. solani* | Positive | Positive | NG | NG | Positive | Positive | NG | NG |

NG: no growth
Positive: at least 1 colony forming unit (CFU) of growth.

Individual ingredient formulations (A-7 to C-7 and E-7 to G-7) and combinatory components formulation (D-7 and H-7) were tested for antimicrobial activity using standard procedural methodology (International Standards Organization). Minimum inhibitory concentrations (MICs) were defined as the lowest concentration of antimicrobial that will inhibit the visible growth of a micro-organism after incubation. MICs are used by diagnostic laboratories and as a research tool to determine the in vitro activity of new antimicrobials. In this particular set of MIC assays, either one or more of the active components of the novel formulation were added (100 µl) to an innoculum (10 ml) of a Gm+ (*Staphylococcus aureus*), Gm− (*Pseudomonas aeruginosa*), or fungi (*Candida albicans, Fusarium albicans*) each at an approximate concentration of 1.0E+04-1.0E+06 CFU/ml. After a 24 hour contact time, a sample of each test tube was plated on media specific to each bacteria or fungi, and growth was recorded. Growth of more than one colony on any of the agar plates was considered a failure (positive) of one or more of the components of the novel formulation to kill the microbial innoculum at that selected concentration of the component and/or mixture thereof. MIC testing usually were initiated with higher concentrations of the components and then halted once, by virtue of dilution, the MIC is achieved for each component and/or mixtures thereof.

In the present testing, three active components, stabilized chlorine dioxide, ammonium chloride, and C12-14-alkyl (ethylbenzyl) dimethylammonium chloride were provided either singularly or within a mixture in either a phosphate or borate buffering system. The buffering agents are considered inactive ingredients and provide pH adjustment and tonicity requirements for use in human health care applications and have no purported antimicrobial activity.

Example 8: Formulation is Effective in Killing Infectious Protozoa *Acanthamoeba* Spp Free living amebae of the genus *Acanthamoeba* are saprophytic protozoa that are ubiquitous in the environment.

Particular species of the genus, including *Acanthamoeba castellanii*, can cause severe infections in man. One manifestation of *A. castellanii* infection includes extremely rare opportunistic granulatomas encephalitis that can develop only after accidental oral/nasal insufflation. A more common, albeit rare, disease syndrome includes *Acanthamoeba keratitis* resulting from inadvertent ocular exposure to environmental sources. The latter condition is considered a severe form of keratitis that can lead to long term sequelae including blindness if left untreated. A significant increase of diagnosed cases of *Acanthamoeba keratitis*, particularly among contact lens users, has been observed over the last decade.

There are few options for treatment of *Acanthamoeba keratitis*. Conventional chemotherapeutic agents, including antibiotics and antifungals have no efficacy against this agent. Biocidal agents, including povidone-iodine, polyhexamethylene biguanide (Baquacil), hexamidine, and chlorhexidine, collectively have shown marginal efficacy but are also cytotoxic to the cornea and surrounding tissue.

The anti-protozoal efficacy of a formulation disclosed herein, e.g., STR-325 (comprising stabilized chlorine dioxide, ammonium chloride and C12-14-alkyl(ethylbenzyl) dimethylammonium chloride) against *A. castellanii* trophozoites in an experimental colorimetric assay (McBride, J, Ingram, P R, Henriquez, F L, Roberts, C W. J Clin Microb, February; 43(2):629-34, 2005) was tested. The efficacy against two leading over-the-counter multipurpose solutions (MPS) as comparators was evaluated. The assay in this study used cultured *A. castellanii* trophozoites originating from corneal scrapings and was obtained from ATCC (Manassas, Va.). *A. castellanii* was propagated using specific liquid media (PYG w/inhibitory antibiotics) under sterile conditions. Trophozoites were enumerated using a Coulter cell counter and verified by light microscopy and a hemocytometer. Alamar blue was used as a vitality dye, and effectively measures cellular respiration. The intensity of the dye degraded at an equivalent rate of remaining active trophozoites in solution; thus the reciprocal of the measured absorbance of the dye was correlative to the remaining active trophozoites in the test well. Predetermined concentrations of active trophozoites (1.2E+3 cells/well) were used for the assay, and exactly 25 µl of either STR-325, dilutions thereof, or comparator MPS were aliquoted into *A. castellanii*-loaded wells; testing was performed in sextuplicate (6 wells/solution). Disinfectant-*A. castellanii* solutions were incubated for either 96 or 1 hour and then read on a spectrophometer at 570 nm.

Figure 14A:
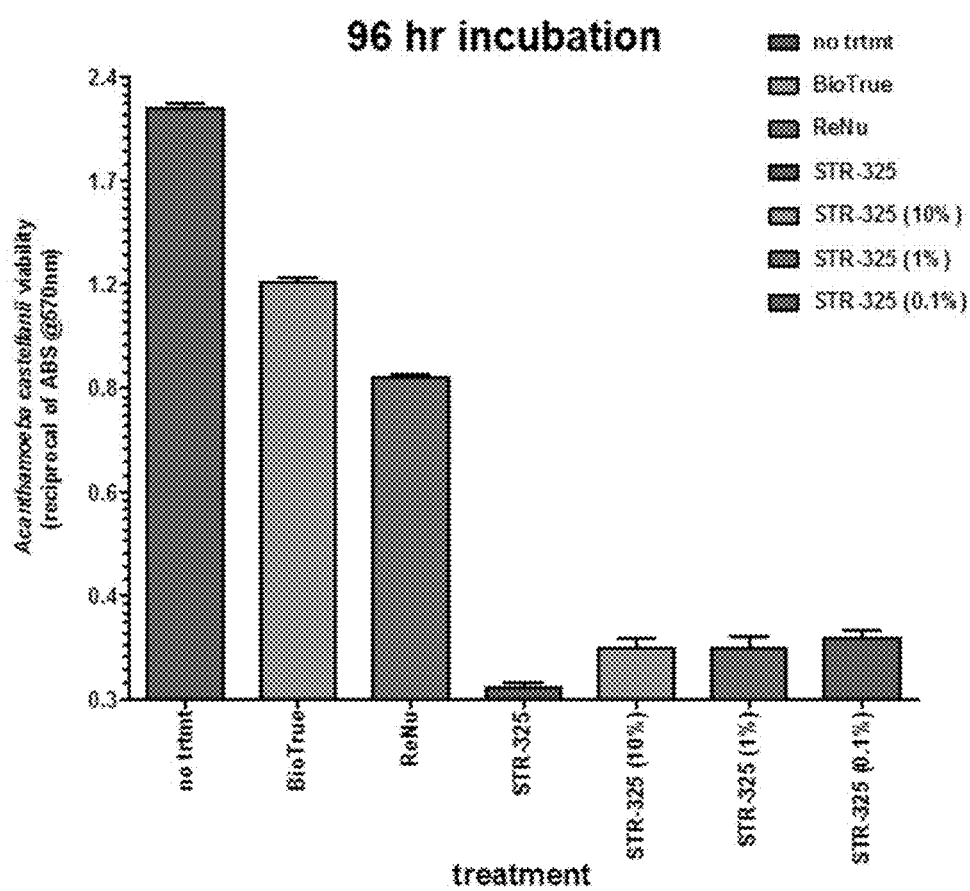
FIG. 14A shows the results of $96h$ incubation of STR-325 and two commercially available multipurpose disinfection solution (ReNu and Biotrue) for *A.castellanii*.
Figure 14B:
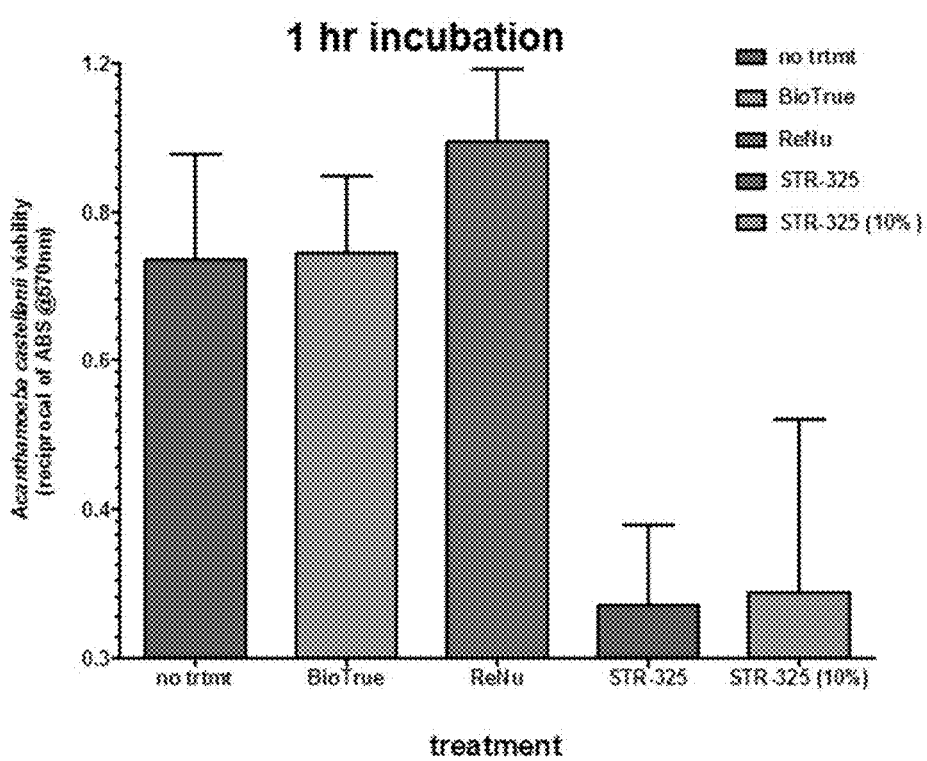
FIG. 14B shows the results of 1 h incubation of STR-325 and two commercially available multipurpose disinfection solution (ReNu and Biotrue) for *A.castellanii*.

Results of the testing are shown in FIG. 14A and FIG. 14B. STR-325 was efficacious in killing all trophozoites at both incubation times, and maintained effectiveness even when serially diluted (1:10). Both comparator solutions (ReNu, Biotrue) had marginal effects on reduction of active trophozoites at 96 hr incubation, and no effect at the shorter (1 hr) incubation time.

Example 9: Exemplary Formulation and Compounding Procedure

The compounding tank was charged with USP water (80% total final volume). The following ingredients were then added: sodium phosphate, monohydrate, monobasic, sodium phosphate, heptahydrate, dibasic, sodium chloride, and potassium chloride. The mixture was stirred for NLT (Not less than) 15 minutes. Tetronic® 908 was slowly added into the compounding tank and mixed until dissolved completed (NLT 30 minutes). The mixture was cooled below 45 C and the following ingredients were added: ammonium chloride, stabilized chlorine dioxide, and C12-C14-alkyl (ethylbenzyl)dimethylammonium chloride. The resulting mixture was mixed for NLT 30 minutes. The pH and osmolarity were measured (Targeted pH=7.0, and Osmolarity 300). Sterility: use 0.22 µm sterilizing filter (Minipore).

What is claimed is:

1. A method of disinfecting a medical device comprising contacting the medical device with a medical disinfecting composition comprising:
    (a) stabilized chlorine dioxide solution comprising a chlorite salt;
    (b) a quaternary ammonium salt, consisting of C12-C14-alkyl(ethylbenzyl)dimethylammonium chloride;
    (c) ammonium chloride having a formula of $NH_4Cl$; and
    (d) water,
    wherein the C12-C14-alkyl(ethylbenzyl)dimethylammonium chloride is present in an amount ranging from about 0.001% to about 0.1% w/w.

2. The method of claim 1, wherein the chlorite salt is an alkali metal chlorite salt.

3. The method of claim 2, wherein the alkali metal chlorite salt is sodium chlorite.

4. The method of claim 3, wherein the sodium chlorite salt is present in an amount ranging from about 0.0001% to about 0.1% w/w.

5. The method of claim 1, wherein the stabilized chlorine dioxide solution is present in an amount ranging from about 0.005% to about 1.0% w/w.

6. The method of claim 1, wherein the ammonium chloride is present in an amount ranging from about 0.001% to about 2.0% w/w.

7. The method of claim 1, further comprising a buffer to maintain the pH between about 7 and about 8.

8. The method of claim 1, wherein the medical device is in contact with a mammal tissue after contacting the medical device with a medical disinfecting composition.

9. The method of claim 1, wherein the medical device is selected from the group consisting of contact lenses, contact lens cases, surgical instruments, and dental instruments.

* * * * *